US012642865B2

(12) United States Patent
Chiang et al.

(10) Patent No.: US 12,642,865 B2
(45) Date of Patent: Jun. 2, 2026

(54) TOROIDAL MIXED NANOPARTICLE, METHOD FOR PREPARING THE SAME, AND METHOD FOR MULTIFUNCTIONAL DELIVERY USING THE SAME

(71) Applicant: China Medical University, Taichung City (TW)

(72) Inventors: Yi-Ting Chiang, Taichung City (TW); Hui-Chang Lin, Taichung City (TW); Guan-Jhong Huang, Taichung City (TW)

(73) Assignee: China Medical University, Taichung City (TW)

( * ) Notice: Subject to any disclaimer, the term of this patent is extended or adjusted under 35 U.S.C. 154(b) by 639 days.

(21) Appl. No.: 18/057,021

(22) Filed: Nov. 18, 2022

(65) Prior Publication Data

US 2024/0165262 A1 May 23, 2024

(51) Int. Cl.
*A61K 47/69* (2017.01)
*A61K 47/59* (2017.01)
*A61P 35/00* (2006.01)

(52) U.S. Cl.
CPC ........ *A61K 47/6907* (2017.08); *A61K 47/593* (2017.08); *A61P 35/00* (2018.01)

(58) Field of Classification Search
None
See application file for complete search history.

(56) References Cited

FOREIGN PATENT DOCUMENTS

CN         102357075 A   *   2/2012

OTHER PUBLICATIONS

Chen et al. Langmuir 2013 29:8417-8126 (Year: 2013).*
Yang et al. Angewandte Chemie 2017 129:5638-5642 (Year: 2017).*
Cui et al. Soft Matter 2009 5:1269-1278 (Year: 2009).*
Zhou et al. ACS Macro Letters 2016 5:1266-1272 (Year: 2016).*
Nishiyama et al. Cancer Research 2003 63:8977-8983 (Year: 2003).*
Zhang et al. Colloids and Surfaces A: Physicochemical and Engineering Aspects 2021 622(126669):1-8 (Year: 2021).*
Wang et al. Journal of Microencapsulation 2019 36(6):552-565 (Year: 2019).*

* cited by examiner

*Primary Examiner* — Melissa S Mercier
*Assistant Examiner* — Caralynne E Helm
(74) *Attorney, Agent, or Firm* — HSML P.C.

(57) ABSTRACT

Provided is a toroidal mixed nanoparticle including a first polymer and a second polymer interacting with the first polymer. Also provided is a method for preparing the toroidal mixed nanoparticle, including mixing the first polymer and the second polymer having cleavable hydrophobic groups to form a mixed nanoparticle; and removing a portion of cleavable hydrophobic groups from the second polymer to make the second polymer charged and to form the toroidal mixed nanoparticle. Further provided is a method for delivering a drug or a bioactive agent to a subject in need thereof, including administering to the subject a pharmaceutical composition that includes the toroidal mixed nanoparticle conjugated to an effective amount of the drug or the bioactive agent, and a pharmaceutically acceptable excipient thereof.

11 Claims, 26 Drawing Sheets
(16 of 26 Drawing Sheet(s) Filed in Color)

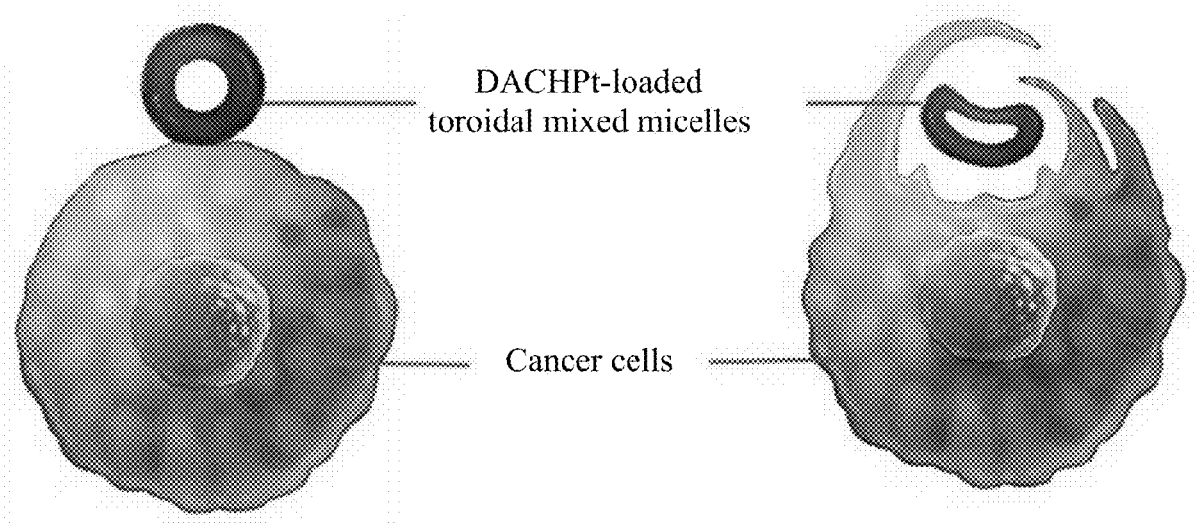
DACHPt-loaded
toroidal mixed micelles
Cancer cells
FIG. 5B
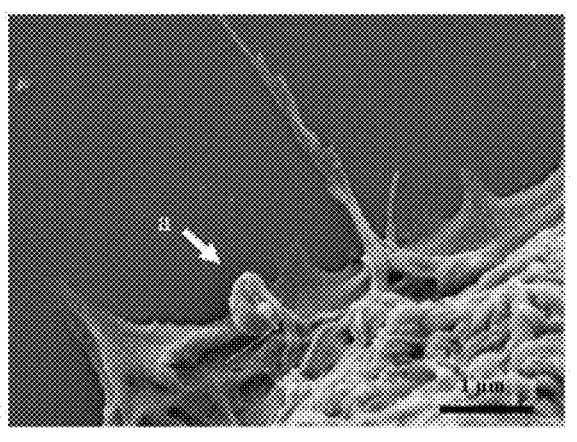
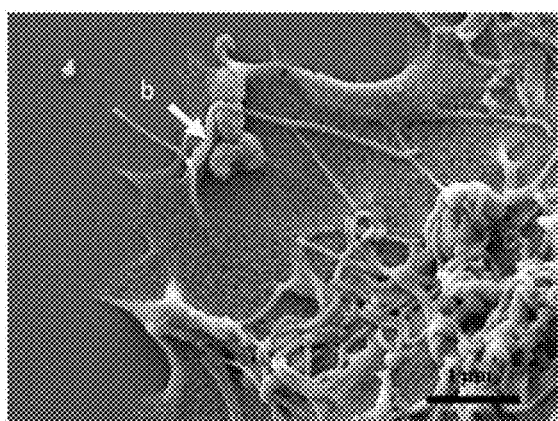
FIG. 5C-1          FIG. 5C-2

DACHPt-loaded spherical micelles

DACHPt-loaded toroidal micelles

DACHPt-loaded spherical micelles

DACHPt-loaded toroidal micelles

DACHPt-loaded spherical micelles

DACHPt-loaded toroidal micelles

DACHPt-loaded spherical micelles

DACHPt-loaded toroidal micelles

DACHPt-loaded spherical mixed micelles

DACHPt-loaded toroidal mixed micelles

DACHPt-loaded spherical mixed micelles

DACHPt-loaded toroidal mixed micelles

TOROIDAL MIXED NANOPARTICLE, METHOD FOR PREPARING THE SAME, AND METHOD FOR MULTIFUNCTIONAL DELIVERY USING THE SAME

BACKGROUND

Technical Field

The present disclosure relates to nanotechnology, particularly to a multifunctional delivery system using a mixed nanoparticle.

Description of Related Art

Life expectancy has significantly increased. Hence, the incidence of various age-related diseases has increased and received great attentions, such as cancer, blood pressure, diabetes, hyperlipidemia, heart disease, stroke, osteoporosis and degenerative arthritis. However, some drugs show low specificity and off-target effects. For example, the use of anti-cancer drugs may be accompanied by side effects such as vomiting, nausea, fatigue and leukopenia. Therefore, the development of the drug delivery system with high specificity, good penetration, and flexibility is urgently needed.

Although many drug delivery systems have been developed in the art, there are still many problems to be solved. For example, some drug delivery systems showed low stability, insufficient elasticity (poor penetration ability). Moreover, some drug delivery systems display only little penetration effects for tumor and vessel, indicating drugs cannot reach and accumulate in tumor lesions. Furthermore, some drug delivery systems are lacking flexibility for conjugating drugs or biological agents according to actual needs. Further taking micelles as example, these systems have been used with varying degrees of success, e.g., in preclinical models, poor solubility in water miscible solvents, and relatively high critical micellar concentrations causes the micelles to fall apart rapidly when used in vivo.

Thus, there is an unmet need in the art to develop a nanoparticle for multifunctional delivery and to construct a system using the same capable of carrying drugs or biological agents, so as to solve the above problems in the field and meet the clinical needs.

SUMMARY

Given the foregoing, the present disclosure provides a toroidal mixed nanoparticle comprising a first polymer and a second polymer interacting with the first polymer.

In at least one embodiment of the present disclosure, the toroidal mixed nanoparticle is a toroidal mixed micelle.

In at least one embodiment of the present disclosure, the toroidal mixed nanoparticle has a diameter of from about 50 nm to about 1200 nm, e.g., about 50 nm, 100 nm, 200 nm, 300 nm, 400 nm, 500 nm, 600 nm, 700 nm, 800 nm, 900 nm, 1000 nm, 1100 nm, or 1200 nm, but the present application is not limited thereto. In some embodiments, the toroidal mixed nanoparticle has a diameter of from about 50 nm to about 500 nm, 50 nm to 220 nm, or, 100 nm to 200 nm.

In at least one embodiment of the present disclosure, the toroidal mixed nanoparticle has elasticity.

In at least one embodiment of the present disclosure, the interaction between the first polymer and the second polymer is electrical property, hydrophilicity, or hydrophobicity. In some embodiments, the first polymer is an amphiphilic polymer, and the second polymer is a hydrophobic polymer, e.g., the amphiphilic polymer is d-α-tocopherol polyethylene glycol succinate, and the second polymer is a poly-γ-benzyl-1-glutamate, but the present disclosure is not limited thereto. In some embodiments, the first polymer comprises polyethylene glycol.

In at least one embodiment of the present disclosure, the toroidal mixed nanoparticle is conjugated with a drug or a bioactive agent. In some embodiments, the drug or bioactive agent is selected from the group consisting of platinum derivatives, camptothecin, doxorubicin, methotrexate, 17-(Allylamino)-17demethoxygeldanamycin (17-AAG), celecoxib, capecitabine, docetaxel, epothilone B, Erlotinib, Etoposide, GDC0941, Gefitinib, Geldanamycin, Imatinib, Intedanib, lapatinib, Neratinib, NVP-AUY922, NVP-BEZ235, Panobinostat, Pazopanib, Ruxolitinib, Saracatinib, Selumetinib, Sorafenib, Sunitinib, Tandutinib, Temsirolimus, Tipifarnib, Tivozanib, Topotecan, Tozasertib, Vandetanib, Vatalanib, Vemurafenib, Vinorelbine, Vismodegib, Vorinostat, ZSTK474, and any combination thereof, but the present disclosure is not limited thereto. In some embodiments of the present disclosure, the platinum derivatives may be dichloro(1,2-diaminocyclohexane) platinum(II) (DACHPt), but the present disclosure is not limited thereto.

The present disclosure also provides a method for preparing the toroidal mixed nanoparticle mentioned above, comprising mixing a first polymer and a second polymer to form a mixed nanoparticle, wherein the second polymer has cleavable hydrophobic groups; and removing a portion of the cleavable hydrophobic groups from the second polymer to make the second polymer charged and to form the toroidal mixed nanoparticle.

In at least one embodiment of the present disclosure, the cleavable hydrophobic groups may be benzyl group, fluorenylmethoxycarbonyl protecting group (Fmoc), tert-butoxycarbonyl protecting group (Boc), or any combination thereof, but the present disclosure is not limited thereto.

In at least one embodiment of the present disclosure, the first polymer and the second polymer are dissolved in the solution, and the mixed nanoparticle is formed via a solvent-exchange method.

In at least one embodiment of the present application, the mixed nanoparticle is reacted with acid or base to remove the portion of the cleavable hydrophobic groups from the second polymer. In some embodiments, the mixed nanoparticle is reacted with alkali, e.g., NaOH.

In at least one embodiment of the present application, the mixed nanoparticle is reacted with acid or base for about 2 hours to about 72 hours, e.g., about 2 hours, 4 hours, 8 hours, 12 hours, 16 hours, 20 hours, 24 hours, 28 hours, 32 hours, 36 hours, 40 hours, 44 hours, 48 hours, 52 hours, 56 hours, 60 hours, 64 hours, 68 hours, or 72 hours, but the present application is not limited thereto. In some embodiments, the mixed nanoparticle is reacted with alkali for about 2 to 72 hours, 24 to 72 hours, or 24 to 36 hours.

In at least one embodiment of the present disclosure, about 10% to about 50% (e.g., about 10%, 12%, 14%, 16%, 18%, 20%, 25%, 30%, 35%, 40%, 45%, or 50%), about 20% to about 50%, or about 25% to about 35% of the cleavable hydrophobic groups are removed from the second polymer, but the present application is not limited thereto.

The present disclosure also provides a method for delivering a drug or a bioactive agent to a subject in need thereof, comprising providing a pharmaceutical composition that includes the toroidal mixed nanoparticle mentioned above, an effective amount of the drug or the bioactive agent conjugated to the toroidal mixed nanoparticle, and a pharmaceutically acceptable excipient; and administering the pharmaceutical composition to the subject. In at least one embodiment of the present application, the subject suffers from cancer.

In summary, the present disclosure provides a novel and multifunctional delivery system using toroidal mixed nanoparticle. The multifunctional delivery system is easy to use and shows high stability and biosafety. With the extraordinary elasticity, the toroidal nanoparticle used in the present disclosure can penetrate the blood vessels and accumulate into tumor lesions. Multifunctional delivery system provided herein shows the flexibility for selecting the drugs or biological agents, such as anti-cancer drug, and synergistically enhances the therapeutic effects thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will become more readily appreciated by reference to the following descriptions in conjunction with the accompanying drawings.

FIG. 4F shows stability tests. The toroidal nanoparticles (TNs) and DACHPt-loaded toroidal mixed micelles were incubated at 37° C. for 1 and 6 h. The particle sizes were determined by dynamic light scattering (DLS) and the statistical analysis was compared with the sizes at 0 h in 37° C.

FIGS. 5A to 5E show internalization in static state. The micelles in bright green are indicated by the white arrow. FIG. 5A shows the real-time monitoring images of the FITC-labeled DACHPt-loaded spherical polymeric and toroidal mixed micelles in HCT116 human colon cancer cells. The cell membranes were previously stained and the stained cellular membrane is represented in red; the FITC-labeled mixed micelles are shown in green. These photos were taken and collected from a real-time video. The contact orientation of DACHPt-loaded toroidal mixed micelles to cells was schematically illustrated (shown in FIG. 5B). The morphologies of the DACHPt-loaded toroidal micelles in the HCT116 human colon cancer cells were observed via SEM images after fixation (shown in FIGS. 5C-1 and 5C-2). The internalization upon time was conducted via flow cytometry to analyze the relative fluorescent intensity of the FITC-labeled DACHPt-loaded spherical polymeric mixed micelles and DACHPt-loaded toroidal mixed micelles after incubation with human colon cancer cell line HCT116 at 37° C. for 1, 3, and 6 h (shown in FIG. 5D). The real-time monitoring images of the FITC-labeled DACHPt-loaded toroidal mixed micelles in RAW 264.7. murine macrophage cell line from the videos (shown in FIG. 5E). The cell membranes were previously stained and represented in red. The FITC-labeled particles are shown in green.

DETAILED DESCRIPTION OF THE EMBODIMENTS

Figure 1:
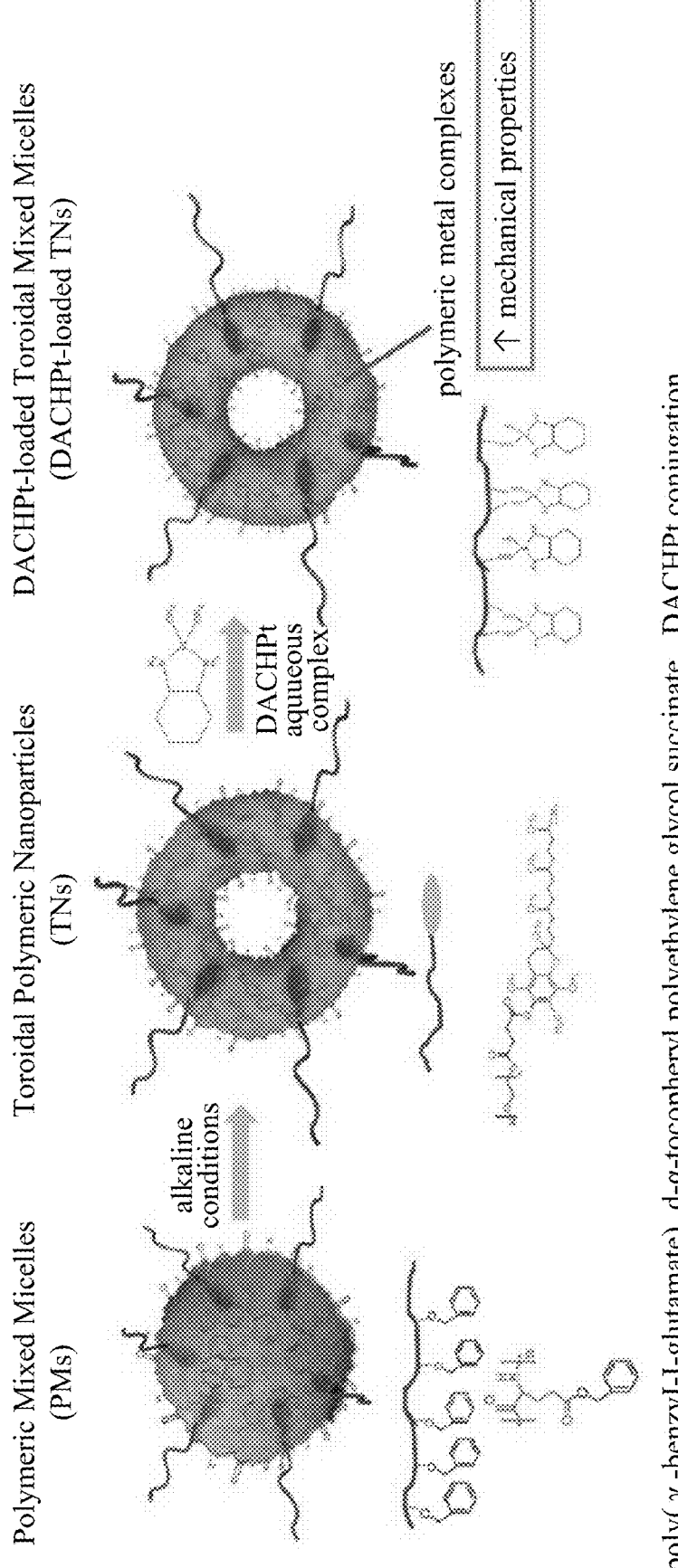
FIG. 1 is a schematic diagram illustrating preparation of dichloro(1,2-diaminocyclohexane) platinum(II) (DACHPt)-loaded toroidal micelles in accordance with embodiments of the present disclosure.

The following embodiments are provided to illustrate the present disclosure in detail. A person having ordinary skill in the art can easily understand the advantages and effects of the present disclosure after reading the disclosure of this specification, and also can implement or apply in other different embodiments. Therefore, it is possible to modify and/or alter the following embodiments for carrying out this disclosure without contravening its scope for different aspects and applications, and any element or method within the scope of the present disclosure disclosed herein can combine with any other element or method disclosed in any embodiments of the present disclosure.

Definitions

The articles "a" "an", and "the" are used herein to refer to one or to more than one (i.e., to at least one) of the grammatical object of the article. The term "or" is used interchangeably with the term "and/or" unless the context clearly indicates otherwise.

As used herein, the term "about" generally referring to the numerical value meant to encompass variations of ±20%, ±10%, ±5%, ±1%, ±0.5%, or ±0.1% from a given value or range. Such variations in the numerical value may occur by, e.g., the experimental error, the typical error in measuring or handling procedure for making compounds, compositions, concentrates, or formulations, the differences in the source, manufacture, or purity of starting materials or ingredients used in the present disclosure, or like considerations. Alternatively, the term "about" means within an acceptable standard error of the mean when considered by one of ordinary skill in the art. Unless otherwise expressly specified, all of the numerical ranges, amounts, values and percentages such as those for quantities of materials, durations of time periods, temperatures, operating conditions, ratios of amounts, and the likes disclosed herein should be understood as modified in all instances by the term "about."

The numeral ranges used herein are inclusive and combinable, any numeral value that falls within the numeral scope herein could be taken as a maximum or minimum value to derive the sub-ranges therefrom. For example, it should be understood that the numeral range "10-50%" comprises any sub-ranges between the minimum value of 10% to the maximum value of 50%, such as the sub-ranges from 10% to 25%, from 25% to 50%, or from 22.5% to 37.5%. In addition, a plurality of numeral values used herein can be optionally selected as maximum and minimum values to derive numerical ranges. For instance, the numerical ranges of 50 nm to 500 nm, 50 nm to 1200 nm, and 500 nm to 1200 nm can be derived from the numeral values of 50 nm, 500 nm, and 1200 nm.

As used herein, "subject" is used to mean any vertebrate including, but not limited to, humans, mammals such as deer, mule, elk, mule deer, seeking to improve a condition, disorder, or disease. However, advantageously, the subject is a mammal such as a human, or an animal mammal such as a domesticated mammal, e.g., a dog, a cat, a horse, a rat, a mouse, or the like, or a production mammal, e.g., a cow, a sheep, a pig, a deer, or the like.

The terms "comprise," "comprising," "include," "including," "have," "having," "contain," "containing," and any other variations thereof are intended used herein to cover a non-exclusive inclusion. For example, when describing an object "comprises" a limitation, unless otherwise specified, it may additionally include other ingredients, elements, components, structures, regions, parts, devices, systems, steps, or connections, etc., and should not exclude other limitations.

As used herein, "administer," "administration," "treatment," "supplementation," "injection," or "provide" refers to a technique used to deliver a substance, i.e., stem cells into the body systemically or locally, or any combination thereof. When administering a therapeutically effective amount of the present invention parenterally or intravenously, it is generally formulated in a unit dosage form (e.g., emulsion, pills, and ointment).

The term "treating" or "treatment" refers to administration of an effective amount of a therapeutic agent to a subject in need thereof, who has the disease, or a symptom or predisposition toward such a disease, with the purpose of cure, alleviate, relieve, remedy, or ameliorate the disease, the symptoms of it, or the predisposition towards it. Such a subject can be identified by a health care professional based on results from any suitable diagnostic method.

As used herein, the term "amphiphilic" is used herein to mean a substance containing both hydrophilic or polar (water-soluble) and hydrophobic (water-insoluble) groups.

The term "hydrophilic" refers to the tendency of a material to disperse freely in aqueous media. A material is considered hydrophilic if it prefers interacting with other hydrophilic material and avoids interacting with hydrophobic material. "Hydrophilicity" used herein may be a relative term, i.e., the same molecule could be described as hydrophilic or not depending on what it is being compared to. In at least one embedment of the present application, the polymer has cleavable hydrophilic groups that can be removed via a chemical reaction such as acid or base treatment, and the hydrophilicity of the polymer is reduced when part of the hydrophilic groups is removed therefrom; however, the polymer still belongs to the hydrophilic compound as defined herein. In some embodiments, hydrophilic molecules are polar and/or charged and have good water solubility, e.g., are soluble up to 0.1 mg/mL or more, but the present disclosure is not limited thereto.

As used herein, the term "hydrophobic" refers to the tendency of a material to avoid contact with water. A material is considered hydrophobic if it prefers interacting with other hydrophobic material and avoids interacting with hydrophilic material. "Hydrophobicity" used herein may be a relative term, i.e., the same molecule could be described as hydrophobic or not depending on what it is being compared to. In at least one embedment of the present application, the polymer has cleavable hydrophobic groups that can be removed via a chemical reaction such as acid or base treatment, and the hydrophobicity of the polymer is reduced when part of the hydrophobic groups is removed therefrom; however, the polymer still belongs to the hydrophobic compound as defined herein. In some embodiments, hydrophobic molecules are nonpolar and/or uncharged and have poor water solubility, e.g., are insoluble down to 0.1 mg/mL or less, but the present disclosure is not limited thereto.

The term "delivery system" refers to a method or process of administering a pharmaceutical compound or bioactive agent to achieve a therapeutic effect in subject in need thereof.

The term "particle" refers to a nano- or micro-sized supramolecular structure comprised of an assembly of molecules. For example, in some embodiments, the amphiphilic block polymer forms a particle in aqueous solution. In some embodiments, particle formation by the amphiphilic block polymer is dependent on pH or temperature.

EXAMPLES

Materials and Animals

Polymers, including d-α-tocopherol polyethylene glycol 1000 succinate (TPGS) and poly(γ-benzyl-1-glutamate) (PBLG), and the anticancer reagent, dichloro(1,2-diamino-cyclohexane)platinum(II) (DACHPt), were all purchased from Sigma-Aldrich (St. Louis, M.O., U.S.A.). The organic solvents, N,N-dimethylacetamide (DMAc) and dimethylformamide (DMF), were both obtained from Duksan Pure Chemical Co., LTD. (Gyeonggido, South Korea), and the o-phenylenediamine (OPDA) reagent used to quantify the platinum reagent was purchased form Alfa Aesar (Ward Hill, M.A., U.S.A.). The dialysis bags were acquired from Rainbow Biotechnology Co., LTD. (Taipei City, Taiwan). The staining reagent for preparing the transmission electron microscopic samples, sodium phosphotungstate (PTA), and the analytical reagents, including dimethyl sulfoxide (DMSO-d6) for hydrogen nuclear magnetic resonance ($^1$H-

NMR) measurements and the potassium bromide (KBr) for Fourier-transform infrared spectroscopic (FT-IR) analysis, were also purchased from Sigma-Aldrich. Sodium hydroxide (NaOH) for nanoparticle preparation and the sodium chloride (NaCl) for stability testing and drug releasing profiles were, respectively, acquired from Uniregion Bio-Tech Inc. and Vetec of Sigma-Aldrich. The dialysis bags and PD-10 desalting columns for purification were, respectively, purchased from Merck Millipore (Burlington, M.A., U.S.A.) and GE Healthcare Life Science (Uppsala, Sweden). The fluorescent dyes, including 5/6-carboxyfluorescein succinimidyl ester (FITC-NHS ester), Cellmask Orang and Cell-Tracker™ Red CMTPX dye were obtained from Thermo Fisher Scientific Inc. (Waltham, M.A., U.S.A.). The cell media, including Dulbecco's modified Eagle's medium (DMEM), McCoy's 5a medium, fetal bovine serum (FBS), and penicillin-streptomycin solution, for the cell culture were acquired from Cytiva (Marlborough, M.A., U.S.A.). The edocytosis inhibitors including amiloride and methyl-β-cyclodextrin (methyl-β-CD) were purchased from Merck and Co. (Rahway, N.J., U.S.A.) and sucrose were obtained from J.T. Baker (Radnor, P.A., U.S.A.). The p-Slide I Luer flow channel chips, polymer coverslip bottom cell-cultured dishes and bioinert cell-cultured dishes were all purchased from ibidi GmbH (Gewerbehof, Grafelfing, Germany). The 96-well microplate for culturing tumor spheroids were purchased from Corning Inc. (Corning, N.Y, U.S.A.). The reagents for bio-TEM observations, including 2.5% glutaraldehyde, 1% osmium tetroxide, uranyl acetate, and lead citrate, were kindly provided by Nautiagene (Taipei City, Taiwan, R.O.C.). Besides, the reagents for H & E staining and for paraffin embedment were kindly provided from Professor Jiunn-Wang Liao.

The animal tests were approved by Institutional Animal Care and Use Committee (IACUC) in China Medical University (IACUC approval number: CMUIACUC-2020-058) and the BALB/c nude mice for our animal tests were provided by National Laboratory Animal Center (Taipei City, Taiwan, R.O.C.). The materials in our animal tests, including Matrigel and isoflurane were respectively obtained from Merck and Panion & BF Biotech. Inc. (Taiwan). The fluorescence dye, cyanine 5.5 NHS ester was acquired from Lumiprobe (Wan Chai, Hong Kong).

The formalin for tissue fixation was purchased from Sigma-Aldrich. The 4',6-diamidino-2-phenylindole (DAPI)-containing mounting medium, the antibodies for frozen tissue staining, including anti-CD34 and anti-45 primary antibodies and the fluorescent secondary antibodies, including Alexa Fluor®488 and 555-labeled anti-rabbit IgG secondary antibodies were obtained from Abcam PLC (Cambridge, U.K.).

Preparation and Characterization of the DACHPt-Loaded Toroidal Mixed Micelles

The TPGS (2 mg) and PBLG (6 mg) polymers were dissolved in DMAc (16 mL) and assembled into polymeric mixed micelles using the solvent exchange method. The fabricated mixed micelles were concentrated using 3000 RPM. ultrafiltration (M.W.C.O. 10K) for 10 min. The concentrated mixed micellar solution was placed into a sample vial, and 0.337 mL of an NaOH aqueous solution (0.5 N) was dropped into the sample vial. The sample vial was then incubated at 25° C. under stirring for an appropriate reaction period. Afterwards, the solution was placed into dialysis bags (M.W.C.O. 6-8 k) and dialyzed against deionized water overnight. The solution was taken from the dialysis bags, and 0.272 mL of DACHPt aqueous complexes was added. The solution was further reacted for a period at 25° C. under stirring. Once the reaction was terminated, excess DACHPt aqueous complexes were removed with 3000 RPM ultrafiltration (M.W.C.O. 30k) for 10 min. Particle sizes and zeta potentials were measured with dynamic light scattering (DLS) (ZS 90, Malvern, U.K.).

The morphologies of the DACHPt-loaded toroidal mixed micelles were observed with a transmission electron microscope (TEM) (JEM-2100F, JEOL Ltd., Japan) and an atomic force microscope (AFM) (Dimension Icon, Bruker, M.A., U.S.A.). For TEM observations, 10 μL of the sample solutions were dropped onto carbon-coated copper grids and a few minutes later, the solutions were removed from the grids. Afterwards, a staining dye containing 1% sodium phosphotungstate (10 μL) was dropped onto the grids for 1 min. After removal of the excess staining dye, the grids were dried and stored at 25° C. for observations. The observations were conducted with a field emission transmission electron microscope (FE-TEM) under an accelerated voltage of 200 kV. Simultaneously, the element distribution of the DACHPt-loaded toroidal mixed micelles was analyzed via energy-dispersive X-ray spectroscopy (EDS) and the INCA software.

The nanostructures were also characterized with an AFM and analyzed with Nanoscope Analysis software. The sample solutions were dropped onto a silicon wafer that was previously air washed and superficially treated with plasma for 1 min. After drying in a vacuum oven, the silicon wafer was moved to AFM for topological observations and quantitative nanomechanical (QNM) measurements. Monocrystal silicon tips (Brucker, Bruker, M.A., U.S.A.) with a nominal spring constant (kN) of 0.7 N/m were selected as the cantilevers. The Young's modulus was analyzed every 10 points in the particles and calculated with the Hertzian contact model.

Drug-Loading Contents, Efficiency, and Stability, Releasing Profiles

To assess the drug contents and loading efficiency of the DACHPt-loaded toroidal mixed micelles, the prepared DACHPt-loaded toroidal mixed micelles were freeze-dried. They were then weighed and redispersed in 1 mL of 20% NaCl solution. After a 24 h reaction, released platinum was detected and quantified via OPDA methods (Zhang, Weiqi, and Ching-Hsuan Tung. "Redox-responsive cisplatin nanogels for anticancer drug delivery." *Chemical Communications* 54.60 (2018): 8367-8370). Briefly, equal volumes of the DACHPt-loaded TM and OPDA solutions (1.2 mg/mL in DMF) were homogeneously blended, and the mixture was bathed at 80° C. for 10 min. As the mixed solution cooled down to 25° C., the platinum concentration was detected at 703 nm with a UV-vis spectrophotometer (Lambda 265, PerkinElmer, M.A., U.S.A.).

The stability tests and drug releasing profiles were conducted for the comparison of DACHPt-loaded polymeric spherical and toroidal mixed micelles. In advance, the DACHPt-loaded spherical polymeric mixed micelles were prepared as following: the polymers, including TPGS (2 mg) and PBLG (6 mg) were dissolved into DMAc (16 mL) along with 2 mg of DACHPt regents. After dialysis against deionized water, the DACHPt-loaded spherical polymeric mixed micelles spherical polymeric mixed micelles were filtered to remove the excess DACHPt and stored at 4° C. until uses. Their morphology was observed using a transmission electron microscope and physical properties including particle sizes, distributions and their mechanical properties (Young's modulus) were measured following the methods of DACHPt-loaded toroidal mixed micelles. A stability test was then conducted as follows: DACHPt-loaded spherical polymeric mixed micelles (0.5 mL) and DACHPt-loaded toroidal mixed micelles (0.5 mL) were mixed with an equal volume of deionized water. DACHPt-loaded toroidal mixed micelles (0.5 mL) were then additionally blended with equal volume of phosphate buffering saline (PBS) (0.5 mL). At a predetermined time, the DACHPt-loaded spherical polymeric mixed micelle and toroidal mixed micelle sizes were analyzed using DLS to study the stability. The releasing profiles of the DACHPt-loaded spherical polymeric mixed micelles and toroidal mixed micelles were also determined upon incubation at a mimetic physiological environment. DACHPt-loaded spherical polymeric mixed micelles and toroidal mixed micelles were first blended with an equal volume of deionized water or PBS, and the solutions were placed into dialysis bags (MWCO 6-8 k). The dialysis bags were then placed in deionized water or PBS at 37° C. and shaken. At a predetermined time, the released DACHPt solution was collected and quantified using OPDA methods, as mentioned above.

Internalization, Tumor Penetration Assessment in Static State and Cytotoxicity

To assess and compare the internalization of the DACHPt-loaded spherical polymeric mixed micelles and the DACHPt-loaded toroidal mixed micelles, the fluorescent dye (FITC) was conjugated onto these two nanoparticles, respectively. In brief, the amino capping TPGS was first modified by reacting with cysteine via an ester linkage. The modified TPGS-NH$_2$ (2 mg), PBLG (6 mg), and anticancer potent reagent DACHPt (2 mg) were then weighed and dissolved in DMAc (16 mL). After dialysis against deionized water, the DACHPt-loaded polymeric mixed micelles were filtered to remove the excess DACHPt. Afterwards, the fluorescent dye, FITC-NHS ester, was dissolved in DMSO (1 mg/mL), and the solution was blended with DACHPt-loaded spherical polymeric mixed micelles at 25° C. Twenty-four hours later, the solution was passed through a PD-10 desalting column to eliminate the excess fluorescent dye, forming FITC-labeled DACHPt-loaded spherical polymeric mixed micelles. The FITC-labeled DACHPt-loaded toroidal mixed micelles were also prepared following the same procedure. Modified TPGS-NH$_2$ was involved in the toroidal mixed micelle preparation described above, and the amino groups of TPGS-NH$_2$ on the toroidal mixed micelles further reacted with the fluorescent dye, FITC. After passing through the PD-10 desalting column, the FITC-labeled DACHPt-loaded toroidal mixed micelles were complete.

The internalization of FITC-labeled DACHPt-loaded spherical polymeric mixed micelles and toroidal mixed micelles was evaluated with the murine macrophage cell line RAW 264.6 and HCT116 human colon cancer cells. The RAW 264.7 and HCT116 cells ($1 \times 10^5$ cells per well) were seeded on a 6-well plate and incubated, respectively, with DMEM and McCoy's 5a cell culturing medium at 37° C. with a 5% CO$_2$ supply. As the cells were attached, FITC-labeled DACHPt-loaded spherical polymeric mixed micelles and toroidal mixed micelles were independently treated with cells. At 1, 3 and 6 h post-incubation, the FITC-labeled DACHPt-loaded spherical polymeric mixed micelles and toroidal mixed micelles were removed, and the cells were twice washed with PBS. The interior fluorescence of these cells was analyzed via flow cytometry (BD FACSCanto, Becton, Dickinson and Company, East Rutherford, N.J., U.S.A.). The internalization was also observed in real-time by a high speed confocal system (Andor Dragonfly, Oxford Instrument plc, Oxfordshire, U.K.). Murine macrophage RAW 264.7 cells and HCT116 human colon cancer cells ($1 \times 10^5$ cells) were seeded on a coverslip-bottom dish (Ibidi GmbH, Grafelfing, Germany). After the cells were attached onto the dish, they were incubated with CellMask Orange (1 μM) for 10 min to stain the cell membranes. Afterwards, FITC-labeled DACHPt-loaded spherical polymeric mixed micelles and toroidal mixed micelles were independently treated with RAW 264.7 and HCT116 cells, and the cells were simultaneously observed with the confocal system for 2 min. The fluorescence of the FITC-labeled DACHPt-loaded spherical polymeric mixed micelles or toroidal mixed micelles and the cell membrane were, respectively, detected at excitation wavelengths of 488 and 554 nm and emission wavelengths of 520 and 567 nm. To confirm the morphology of DACHPt-loaded toroidal mixed micelles on the surface of the HCT116 cells, the cells after 1 h incubation with DACHPt-loaded toroidal mixed micelles were fixation by a series of dehydration. The cells and DACHPt-loaded toroidal mixed micelles were observed using SEM.

In addition, the endocytosis pathway of DACHPt-loaded spherical polymeric mixed micelles and toroidal mixed micelles into human colon cancer cells HCT116 was also determine using flow cytometry. The HCT116 cells ($1\times10^5$ cells per well) were seeded onto each well on a 6-well plate. Various endocytic inhibitors, including amiloride hydrochloride (1 mM), methyl-β-cyclodextrin (20 mM) and hypertonic sucrose (0.25 M) were treated with HCT116 cells for 30 min; afterwards, the cells were washed thrice with PBS and co-cultured with the FITC-labeled DACHPt-loaded spherical polymeric mixed micelles and toroidal mixed micelles. Two hours later, the cells were washed with PBS, collected and analyzed with flow cytometry. The fluorescence of the cells was compared to that of the cells only treated with FITC-labeled DACHPt-loaded spherical polymeric mixed micelles and toroidal mixed micelles for 2 h.

The cell adhesion was also evaluated. The human colon cancer cells HCT116 ($1\times10^5$ cells/mL) were seeded on each well in a 6-well plate. When the cells were attached, the cells were incubated at 4° C. for 30 min. After pre-cooling the cells, the FITC-labeled DACHPt-loaded spherical polymeric mixed micelles and toroidal mixed micelles were treated with the cells for 0.5 h and afterwards, the cells were washed with PBS twice and cultured at 37° C. Two hours later, the cells were washed with PBS twice and collected. The cellular fluorescence was determined by a flow cytometry.

The penetration into cancer cell spheroid in static state was also under a short-termed observation. Human colon-cancer cells HCT116 ($1\times10^6$ cells/mL) were seeded on a bioinert cell dish and incubated with McCoy's 5a medium at 37° C. with a 5% $CO_2$ supply. Three days later, as the cells clustered together, the cells were further incubated with FITC-labeled DACHPt-loaded spherical polymeric mixed micelles or toroidal mixed micelles. The cells as well as the fluorescence was observed using the real-time by a high speed confocal system. The fluorescence of the FITC-labeled DACHPt-loaded spherical polymeric mixed micelles or toroidal mixed micelles were detected at excitation wavelengths of 488 and emission wavelengths of 520 nm. In addition, the tumor penetration was also tracked for 6 h. Firstly, the human colon-cancer cells HCT116 ($5\times10^3$ cells) were stained with CellTracker™ Red CMTPX Dye and seeded on a 96-well ultra-low attachment plates (Corning Inc., Corning, NY, USA). Three days later, as the cell spheroids formed, the FITC-labeled DACHPt-loaded spherical polymeric mixed micelles or toroidal mixed micelles were treated. The fluorescence of the cell tracker and FITC was detected using IncuCyte S3 cell tracking system (Essen BioScience Inc., Ann Arbor, MI, USA).

The cytotoxicity of the DACHPt and DACHPt-loaded toroidal mixed micelles toward HCT116 human colon cancer cells was evaluated with an MTT assay. Various concentrations (0.16-20 mg/mL) of the DACHPt aqueous complexes and DACHPt-loaded toroidal mixed micelles that were previously adjusted based on the DACHPt concentration were treated with HCT116 human colon cancer cells for 24 h. Cell viability was then determined using an MTT assay.

In Vitro Behaviors Under Flow Conditions

DACHPt-loaded spherical polymeric mixed micelles and toroidal mixed micelles were passed through a microfluidic channel under 0.1 mL/min velocity. The dynamic motion and morphology of the mixed micelles were observed using the real-time by a high speed confocal system. In addition, the interaction with macrophages under flow conditions was also observed using the high speed confocal system and quantified using a flow cytometry. The murine macrophage cells RAW 264.7 ($1\times10^6$ cells/mL) were seeded in a 5-mm-wide, 50-mm-long and 200-μm-high channels on the μ-Slide $I^{0.2}$ Luer chips. As the cells were attached, FITC-labeled DACHPt-loaded spherical polymeric mixed micelles and toroidal mixed micelles were steadily injected into the channel under 0.1 mL/min velocity by syringe pump control (Model Fusion 710, Chemyx Inc., Stanford, TX, USA). Meanwhile, the fluorescence was detected as the FITC-labeled DACHPt-loaded spherical polymeric mixed micelles and toroidal mixed micelles attached onto cells by the confocal system. After 30 min, the cells were collected and the fluorescent intensity within cells was analyzed using a flow cytometry.

FITC-labeled DACHPt-loaded spherical polymeric mixed micelles and toroidal mixed micelles (3 mL) were pressed through 0.22 μm poly(vinylidene fluoride) (PVDF) syringe at a flow rate of 0.1 mL/min, controlled by a syringe pump. After 30 min, the filtered FITC-labeled DACHPt-loaded spherical polymeric mixed micelles and toroidal mixed micelles were collected and their volumes were respectively determined by a cylinder. The fluorescence of the filter mixed micelles was measured and compared to that before filtration to determine the extrusion efficacy.

Tumor Accumulation and Biodistribution

Human colon-cancer cells ($1\times10^7$ cells/mL) were also subcutaneously inoculated into 4-week-old female Balb-c/nude mice. The major and minor axes of the tumors were measured using a caliper rule, and the tumor volume (V) was calculated as $V=(ab^2)/2$, where a and b represent the longest and shortest axes of the tumor, respectively. As the tumor size reached 500 to 1000 mm$^3$, the tumor-inoculated mice were utilized to investigate the biodistribution or tumor accumulation of the DACHPt-loaded spherical polymeric mixed micelles and toroidal mixed micelles. To study the biodistribution, the fluorescent dye Cyanine 5.5-NHS ester was respectively labeled onto the amino-terminated DACHPt-loaded spherical polymeric mixed micelles and toroidal mixed micelles according to the abovementioned method to label the FITC onto the DACHPt-loaded mixed micelles. After purification with dialysis, the Cyanine 5.5-labeled DACHPt-loaded spherical polymeric mixed micelles and toroidal mixed micelles were intravenously administered into 4-week-old HCT116-cell-inoculated Balb-c/nude mice via their tail veins. At 6, 24 h post-injection, the mice were observed via an in vivo imaging system (IVIS Lumina LT Series III, PerkinElmer, M.A., U.S.A.). Afterwards, at 24 h post-injection, the mice were euthanized, and their organs and tumors were excised. Organ and tumor fluorescence was determined using the same IVIS.

In addition, the tumor tissues harvested from the mice i.v. administered with Cyanine 5.5-labeled DACHPt-loaded Spherical polymeric mixed micelles and Toroidal mixed micelles were embedded in the Cryo-Gel and the frozen sections were prepared using a cryostat microtome (Leica CM3050S, Leica Biosystems, Wetzlar, Germany). The blood vessels in the tumor frozen sections were labeled using endothelial cell marker recombinant anti-CD34 primary antibody and Alexa Fluor® 488-labeled anti-rabbit IgG secondary antibody. The frozen sections and the cell nuclei were mounted and stained with DAPI-containing mounting medium. The fluorescence of the cell nuclei, Alexa Fluor®488-labeled blood vessels and Cyanine 5.5-labeled DACHPt-loaded Spherical polymeric mixed micelles, Toroidal mixed micelles were independently detected with the excitation wavelengths of 405, 488 and 640 nm and the appropriate emission wavelength using the confocal laser scanning system.

The liver sections were also harvested, frozen in the Cryo-Gel and prepared into slides using a cryostat microtome. The macrophage cells in the liver were labeled using recombinant anti-CD 45 primary antibody and Alexa Fluor® 555-labeled anti-rabbit IgG secondary antibody. The frozen sections were mounted with DAPI-containing mounting medium and meanwhile, the cell nuclei were stained with DAPI. The fluorescence of the cell nuclei, Alexa Fluor® 555-labeled blood vessels and Cyanine 5.5-labeled DACHPt-loaded Spherical polymeric mixed micelles and Toroidal mixed micelles were independently detected with the excitation wavelengths of 405, 561 and 640 nm and the appropriate emission wavelength using the confocal laser scanning system.

In Vivo Tumor Inhibition and Toxicity Evaluation

To investigate the efficacy of tumor inhibition, HCT116-cell-bearing 4-week-old female Balb-c/nude mice whose tumor sizes were up to 500 mm³ were separated into 3 groups and each group contained 5 mice. The tumor bearing mice were independently intravenously injected with PBS, 4 mg/mL of DACHPt aqueous complexes, and 4 mg/mL of DACHPt-loaded Toroidal mixed micelles (adjusted on the basis of the DACHPt concentration) at days 0, 2, and 4. The tumor size and weight were monitored every 2 to 3 days for 16-days post-injection. At day 16 post-injection, the mice were all euthanized, and their blood was collected. Meanwhile, the tumor and liver of mice were collected. The tumors were photographed after excluding the extreme ones. The blood samples were centrifugated under 3000 RPM for 10 min to obtain the serum samples for hepatic and renal functional evaluations. The hepatic function was assessed by the aspartate aminotransferase (AST) and alanine aminotransferase (ALT) values; the function of the kidneys was evaluated with the index of blood urea nitrogen (BUN) and creatinine.

The tumors and livers harvested from mice were preserved in 4% formalin overnight and the tumor and livers were embedded in paraffin to form paraffin tissue blocks. Afterwards, the tissues were sliced into 5-μm thick sections using a microtome (Leica RM 2145, Leica, Wetzlar, Germany). These sections were stained with H & E. The histopathological analysis was performed using an optical microscope (Optiphot-2, Nikon, Tokyo, Japan).

Statistical Analysis

Data are shown as the average value and the standard deviations (mean±SD). The result comparison was analyzed with a Student's t-test (Excel, 2010). Differences were considered significant when the p values were less than 0.05, as noted by asterisks (*, $p<0.05$; , $p<0.01$; and *, $p<0.001$).

Figure 2A:
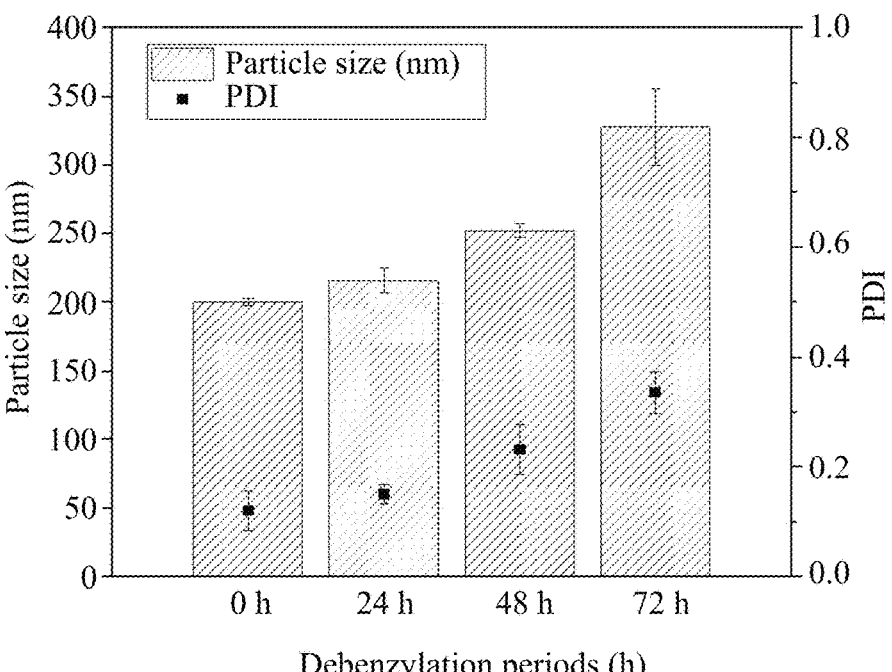
FIGS. 2A to 2D show preparation and characterization of toroid-shaped nanoparticles. Toroidal nanoparticles were prepared via sphere-to-toroid transitions. The polymeric mixed micelles were treated with alkali during various incubation periods. The particle sizes and zeta potentials upon alkaline treatment were recorded (shown in FIGS. 2A and 2B). The values are presented as the mean±S.D. The morphology during incubation periods was also observed via transmission electron microscopy (TEM) and atomic force microscopy (AFM) (shown in FIG. 2C). Moreover, the chemical structures of the constituent polymers were monitored via Fourier transform infrared spectroscopy (FT-IR) (shown in FIG. 2D).
Figure 2B:
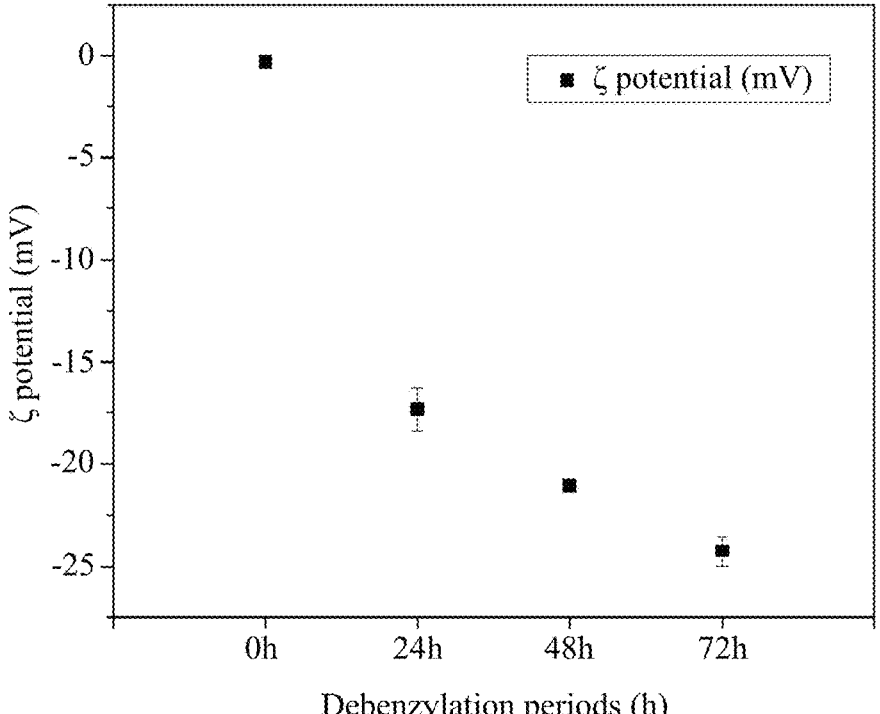
Figure 2C:
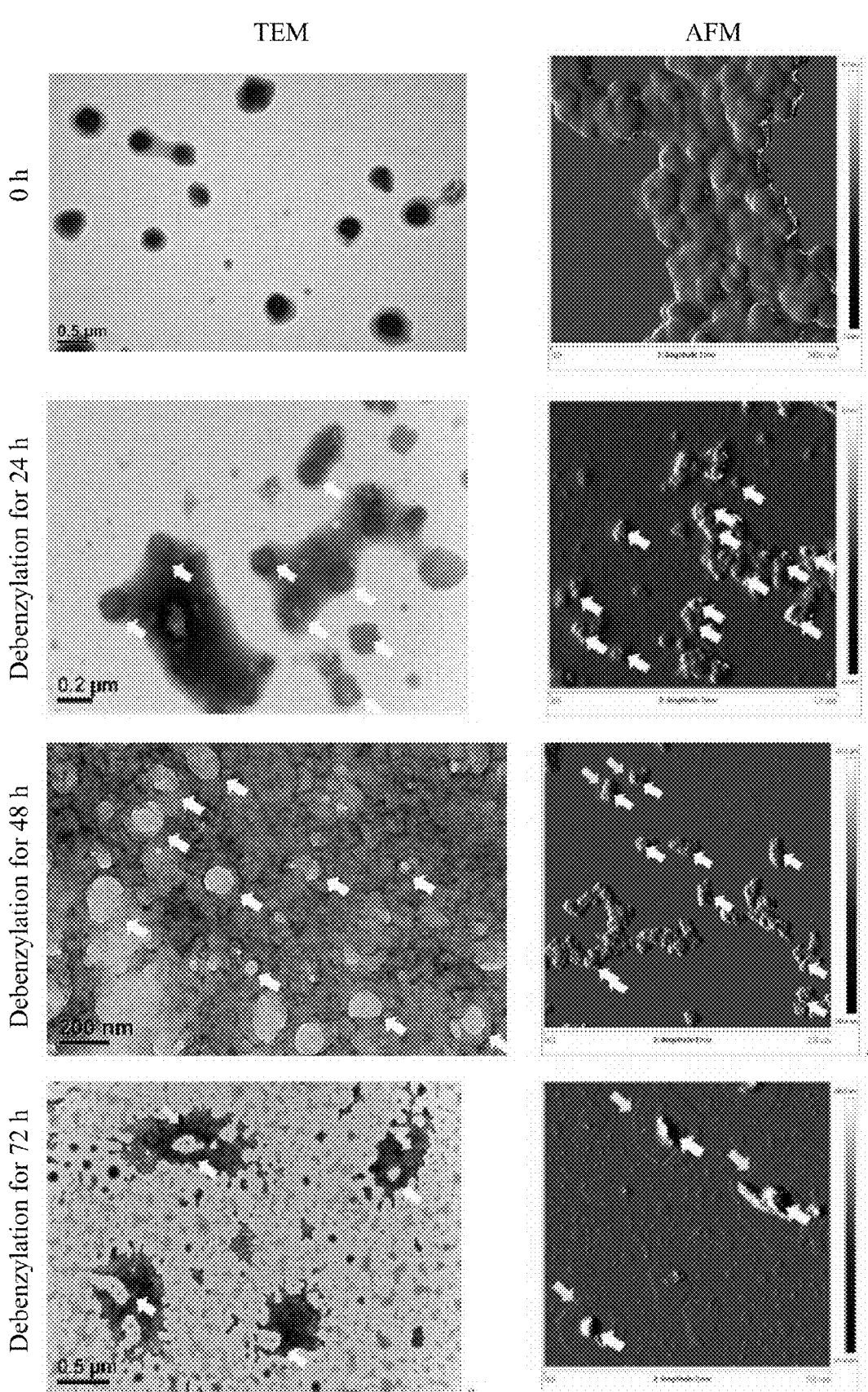
Figure 2D:
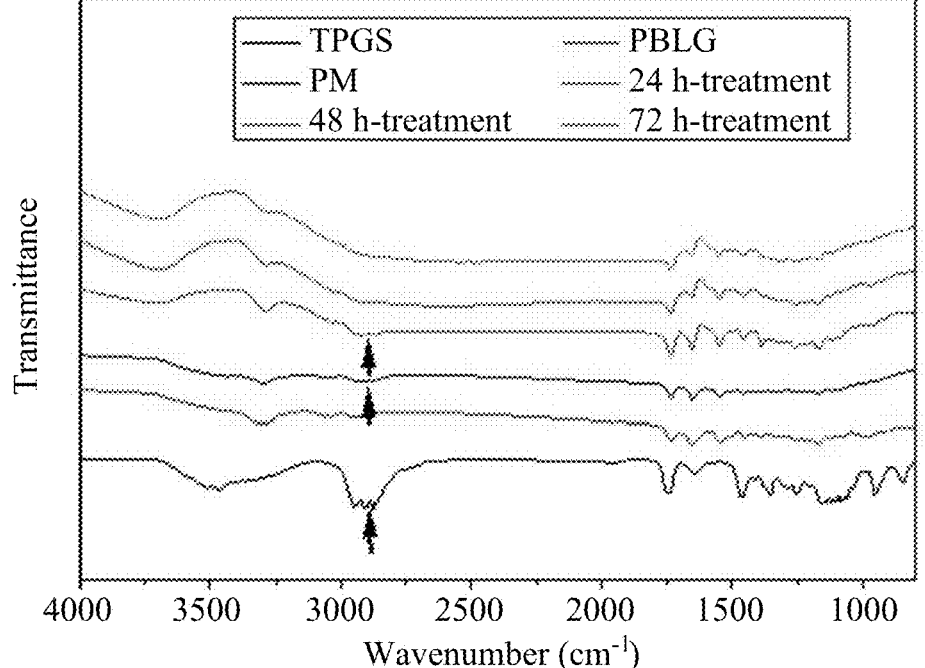

Example 1. Preparation and Characterization of DACHPt-Loaded Toroidal Mixed Micelles The potent anti-colon cancer agent dichloro(1,2-diaminocyclohexane) platinum(II) (DACHPt)), was arranged to conjugate onto these carboxylates, as shown in FIG. 1, forming DACHPt-loaded toroidal mixed micelles (DACHPt-loaded Toroidal mixed micelles). Polymeric mixed micelles (PMs) containing the amphiphilic copolymer TPGS and the hydrophobic polymer PBLG were fabricated via the solvent-exchange method. After concentration via ultracentrifugation, the particle size was determined to be approximately 200 nm, and the polydispersity index (PDI) was around 0.1. Concentrated PMs were then treated with alkali, and the benzyl groups of the PBLG were gradually removed. For optimization, different reactant periods (24, 48, and 72 h) were tested, and the resulting physical properties were evaluated after dialysis against deionized water for removal of the breakages. As shown in FIG. 2A, after undergoing the reaction for 24 h, the debenzylated nanoparticles increased in particle size up to 215.4±9.1 nm; as debenzylation continued over 48 and 72 h, the particle size increased above 250 and 300 nm, and the PDI values were simultaneously raised. The enlargement of the nanoparticles in the alkaline solution was caused by anionic carboxylates, evidenced by the ζ potential presented in FIG. 2B. The ζ potential of the PMs before alkaline treatment was −0.29±0.13 mV; during the incubation period in alkali, the ζ potential of the nanoparticles was negatively increased, as shown in FIG. 2B. During debenzylation, the morphology of the nanoparticles was tuned and observed with a transmission electron microscope (TEM) and an atomic force microscope (AFM), as presented in FIG. 2C. Before alkaline treatment, spherical core-shell PM structures could be clearly observed. After 24 h of alkaline treatment, the toroidal nanoparticles (TNs) were formed. However, with an increasing period in the basic conditions, the toroid-shaped nanoparticles were deformed or driven towards breakage (shown with yellow arrows in FIG. 2C). This could account for the cleavage of the ester in amphiphilic TPGS as suggested by the Fourier transform infrared (FT-IR) spectrum shown in FIG. 2D. In FT-IR spectrum, the peaks from wavenumbers 2850 to 2950 cm⁻¹, representing alkane C—H stretching in TPGS, were gradually diminished in the alkali incubating periods, as the breakage of the TPGS and nanoparticles could only endure 24 h of alkaline treatment for toroidal fabrication. Considering the morphology and chemical structures, 24 h alkaline treatment is suggested as the optimal fabrication time for toroidal nanoparticles.

Figure 3:
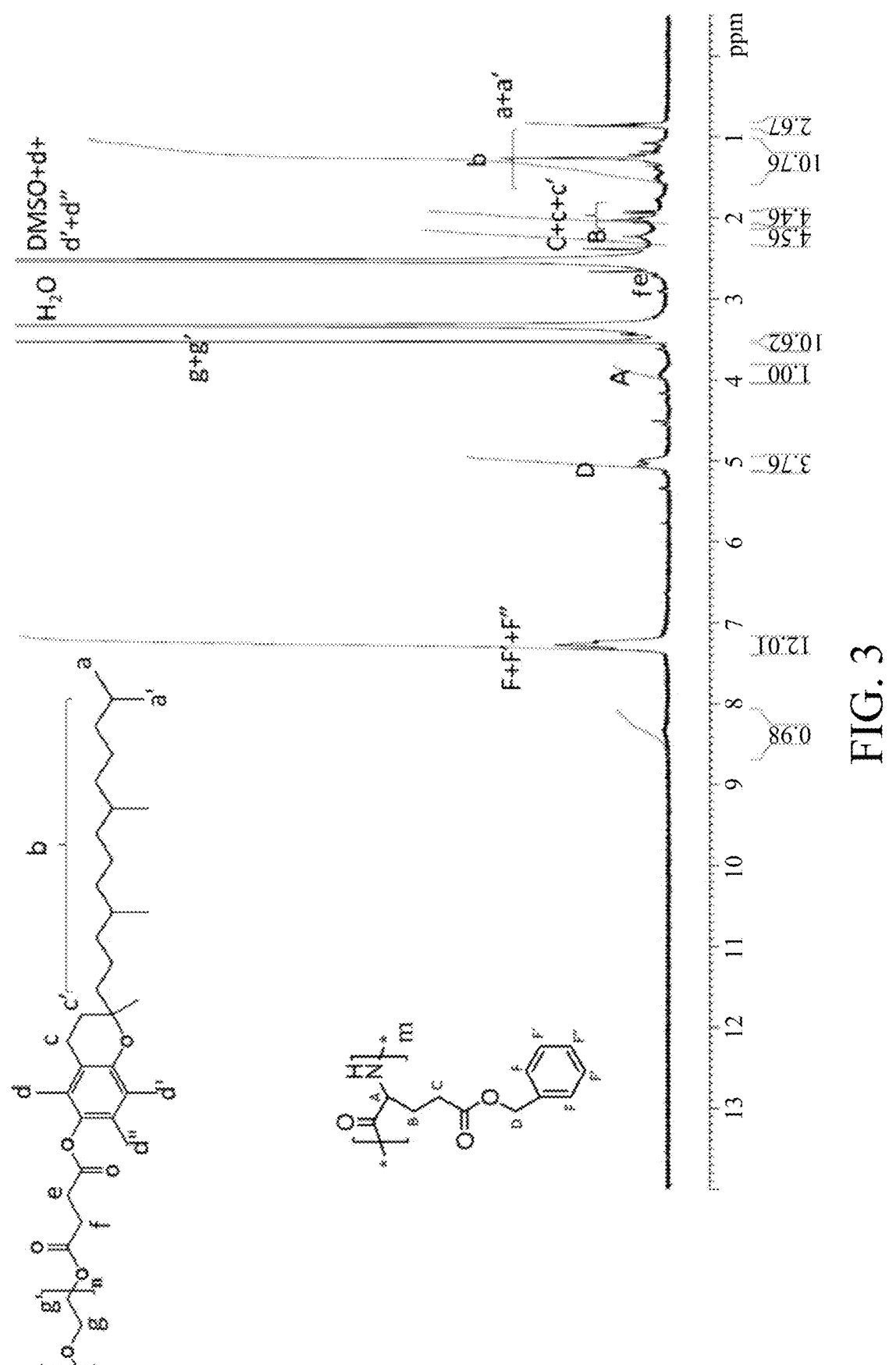
FIG. 3 indicates the $^1$H—N magnetic resonance-spectrum of toroidal nanoparticles, treated with alkali for 24 h. Toroidal nanoparticles after 24 h alkaline treatment were freeze-dried, and the powder was dissolved into the dimethyl sulfoxide-d$_6$ (DMSO-d$_6$) solvent for nuclear magnetic resonance (NMR) measurements.
Figure 4A:
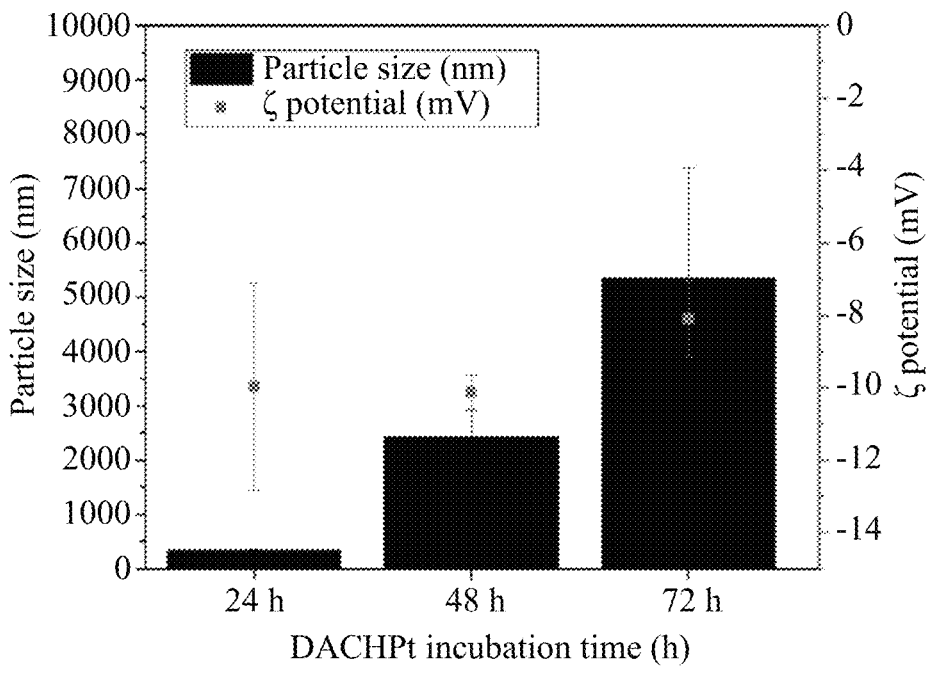
FIGS. 4A and 4B show drug loading of toroidal nanoparticles. DACHPt aqueous complexes were incubated with toroidal nanoparticles for 24, 48, and 72 h. The particle sizes and zeta potentials were monitored during the incubation periods (shown in FIG. 4A). Drug contents and loading efficiency were also measured after the DACHPt-loaded toroidal mixed micelles were freeze-dried (shown in FIG. 4B). The powders were dispersed in 20% saline, and the amount of platinum was determined using the ortho-phenylenediamine (OPDA) methods.
Figure 4B:
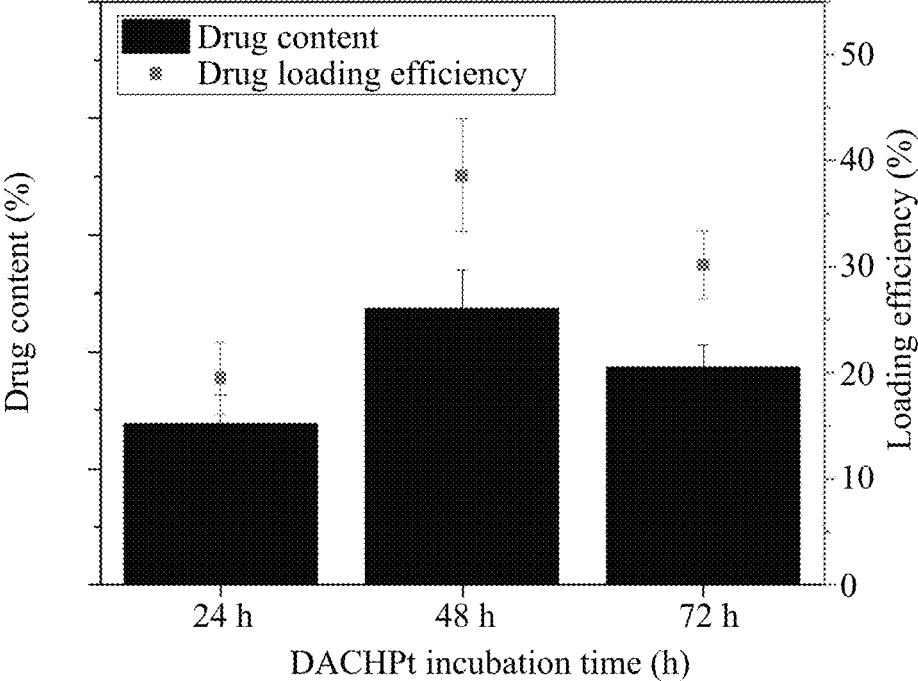

After 24 h alkaline treatment, the ¹H-NMR spectrum (shown in FIG. 3 in the Supporting Information) indicated that approximately 20% of the benzyl groups in PBLG were eliminated, exposing the carboxylates. Those carboxylates provided the location in which to conjugate the potent anticancer drug DACHPt aqueous complexes, whereas TPGS and 80% of the hydrophobic benzyl groups afford the toroid-shaped maintenance. After the incubation of DACHPt aqueous complexes with Toroidal mixed micelles for 24 h, the particle sizes of DACHPt-loaded Toroidal mixed micelles increased up to 336.0±27.3 nm and the ζ potential became approximately −10 mV, as shown in FIG. 4A in the Supporting Information. During the incubation periods over 48 and 72 h, the particle size increased to over 1 m. FIG. 4B in the Supporting Information shows that the drug content and loading efficiency of Toroidal mixed micelles after 24 h treatment with DACHPt aqueous complexes were, respectively, 6.93%±1.22% and 19.52%±3.43%, while the drug content and loading efficiency of Toroidal mixed micelles over 48 h incubation with DACHPt increased. Whilst, taking into account the particle size and further clinical applications in biomedicine, 24 h of incubation time for Toroidal mixed micelles and DACHPt aqueous complexes is acceptable for the conjugation of DACHPt into Toroidal mixed micelles.

Figure 4C:
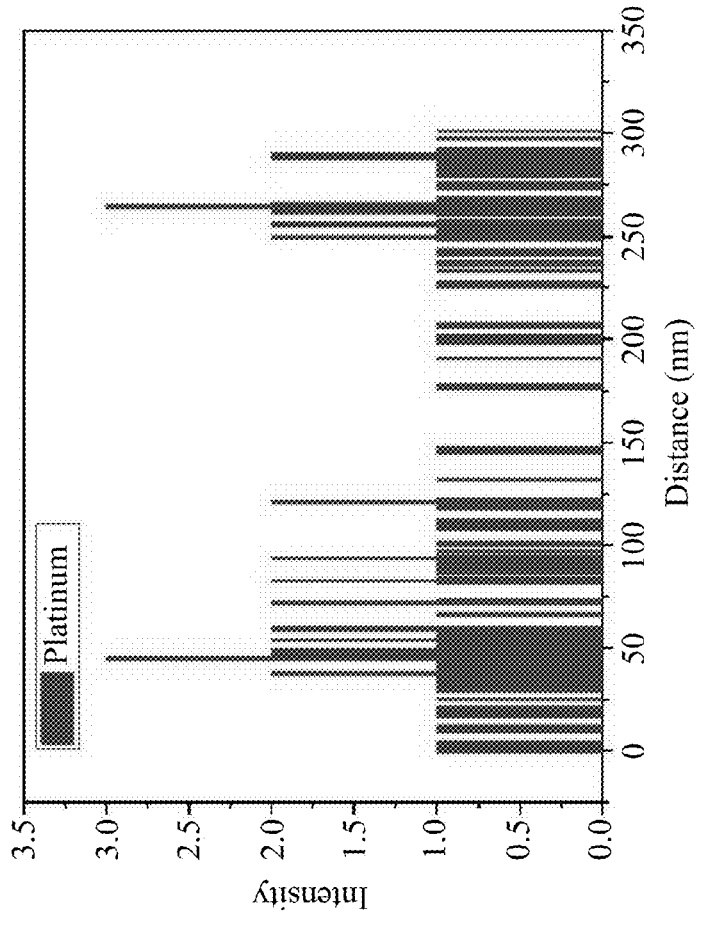
FIGS. 4C to 4F show characterization of the DACHPt-loaded mixed toroidal micelles. The DACHPt-loaded toroidal mixed micelles were analyzed with a scanning electron microscope (SEM) and an AFM to respectively observe the morphology (shown in FIG. 4C) and the tomography of a DACHPt-loaded toroidal mixed micelle and the cross-sectional height of the DACHPt-loaded toroidal mixed micelle (shown in FIG. 4D). The DACHPt-loaded toroidal mixed micelles were also observed via TEM for the morphological observation and analyzed the distribution of the platinum element within DACHPt-loaded toroidal micelles was analyzed with energy-dispersive X-ray spectroscopy (EDS) (shown in FIG. 4E).
Figure 4C:
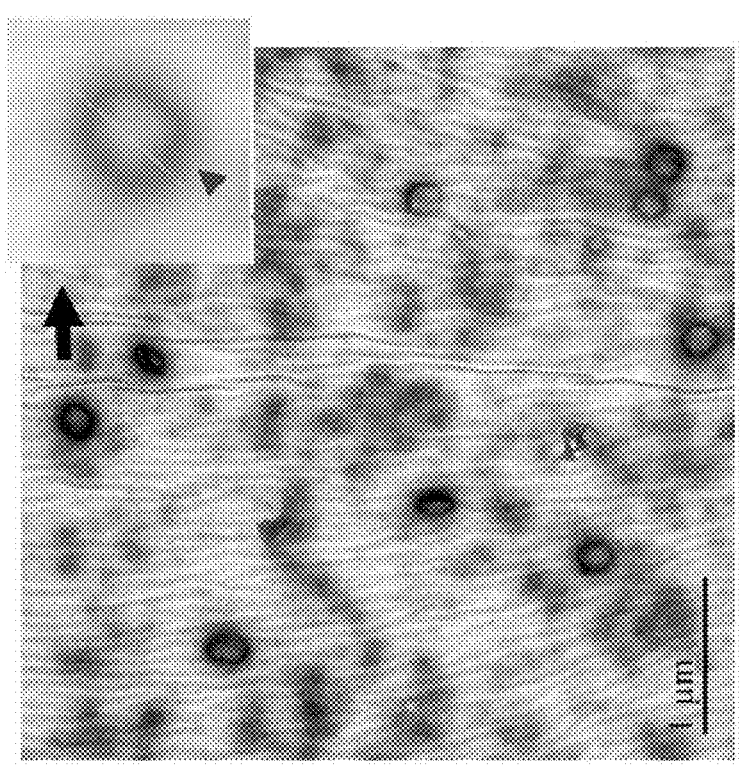
Figure 4D:
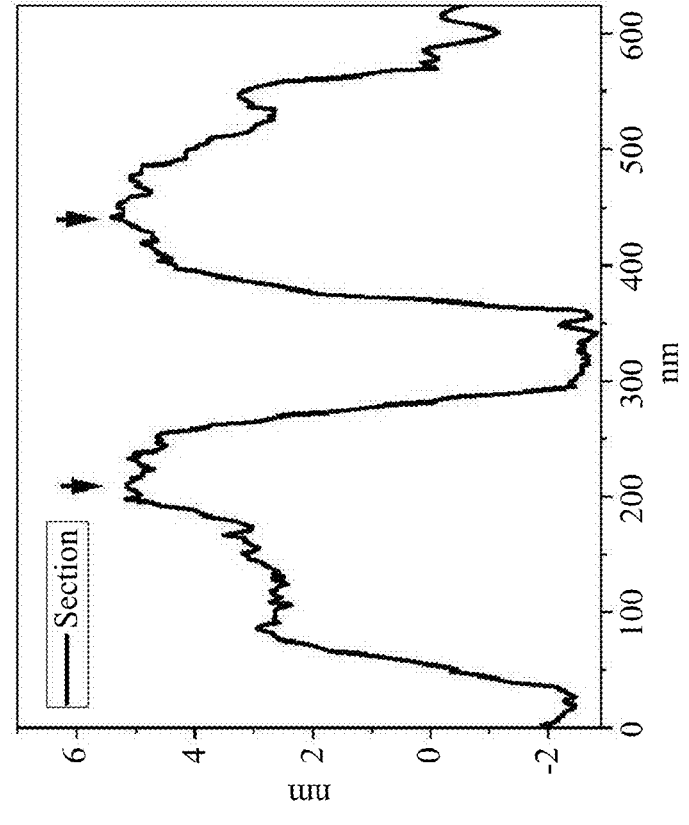
Figure 4D:
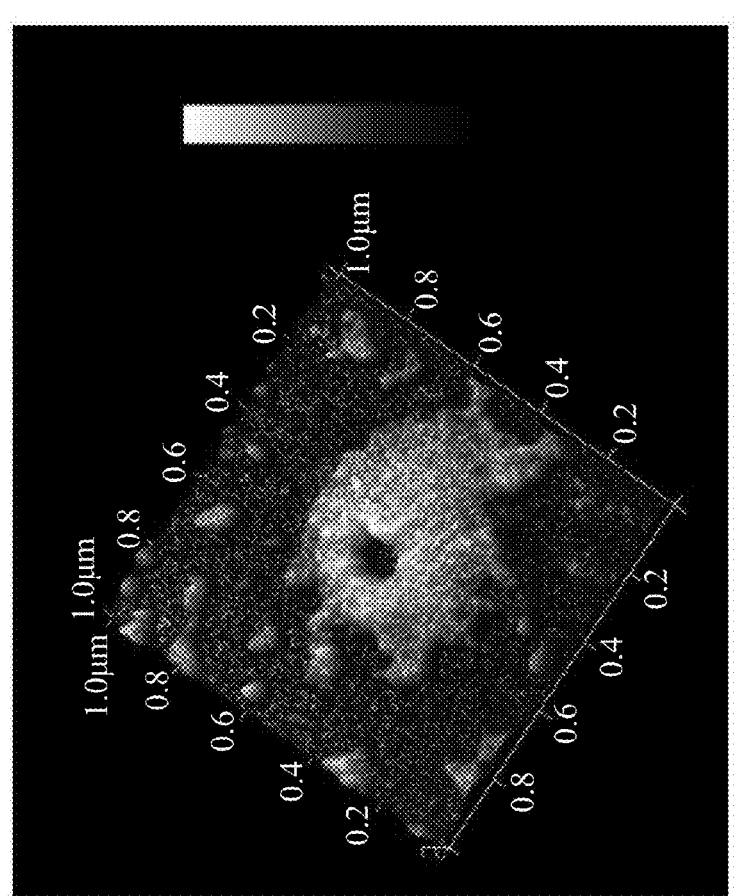
Figure 4E:
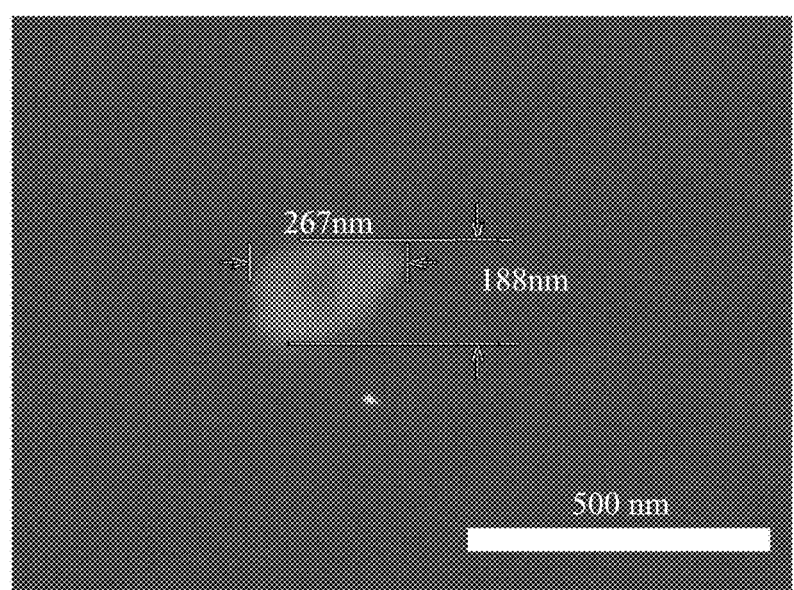

The toroidal architectures and sections of DACHPt-loaded Toroidal mixed micelles characterized by transmission electron microscope images and AFM tomographic images are respectively shown in FIGS. 4C and 4D. The transmission electron microscope images presented in FIG. 4C confirm the toroid-shaped micelles and particle sizes around 300 nm. Notably, the elongated toroidal micelles were also observed in FIGS. 4C to 4E, implying that the transformation ability. The platinum distribution of the anti-cancer reagent DACHPt was also analyzed within the Toroidal mixed micelles using transmission electron microscope and energy-dispersive X-ray spectroscopy (EDS), as shown in FIG. 4C. The DACHPt platinum was identified on the toroidal arms due to the removal of the hydrophobic benzyl groups and the exposure of the carboxylic groups for DACHPt conjugations, forming polymer-metal complexes. Furthermore, the AFM images in FIG. 4D shows the toroid shape and the diameters of the toroidal mixed micelles were around 250 nm, and the heights of the DACHPt-padded mixed micelles were approximately 5 nm. In order to confirm the toroidal nanostructures in aqueous milieus, DACHPt-loaded Toroidal mixed micelles were observed using SEM in water, as FIG. 4E shows. The SEM images displays the elongated toroid-shaped nanoparticle, which were also observed in in FIG. 4C, indicating that our DACHPt-loaded Toroidal mixed micelles preserve their flexibility after forming metal-polymer complexes.

TABLE 1

| Young's modulus of Toroidal mixed micelles and DACHPt-loaded Toroidal mixed micelles. | |
| --- | --- |
| Code | Young's modulus (mPa) |
| Toroidal mixed micelles | 32.458 ± 8.340 |
| DACHPt-loaded Toroidal mixed micelles | 57.591 ± 10.247 *** |

* The Young's modulus of the Toroidal mixed micelles and DACHPt-loaded toroidal mixed micelles was determined by an atomic force microscope (AFM) under quantitative nanomechanical (QNM) mode.

Figure 4F:
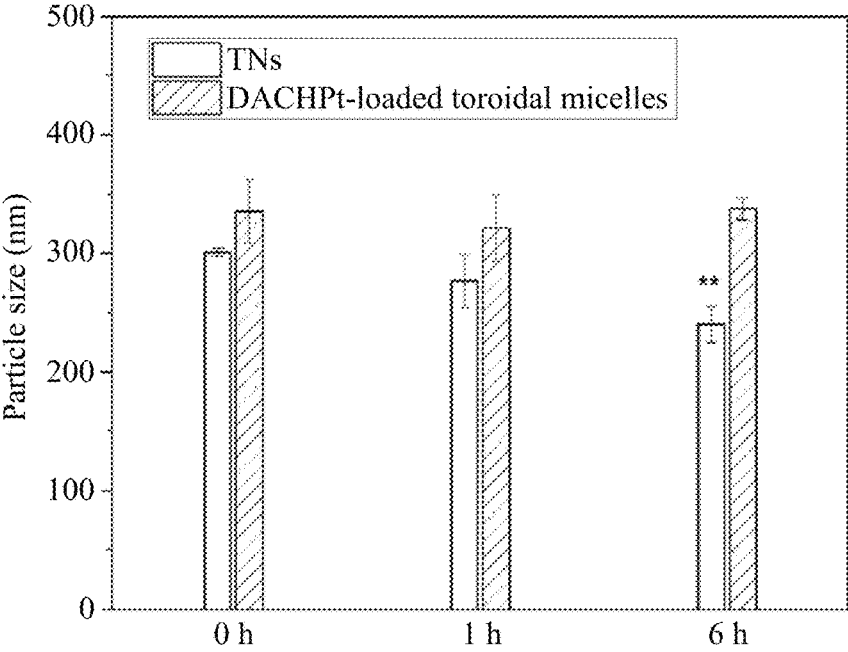

The mechanical properties of the DACHPt-loaded Toroidal mixed micelles were determined via atomic force microscope nano-indentation, as shown in Table 1. The Young's modulus of DACHPt-loaded Toroidal mixed micelles was 32.458±8.340 mPa, which was enhanced by 1.77-fold after the DACHPt aqueous complexes were conjugated. The extent of the increase in Young's modulus indicates that the DACHPt-loaded mixed micelles were able to resist collapse as an external force was applied. As FIG. 4F indicates, after 6 h incubation, the toroidal nanoparticles (TNs) underwent tremendous particle size changes in FIG. 4F. With respect to DACHPt-loaded Toroidal mixed micelles, relatively subtle particle size change was shown. Even though their morphology was observed transform, DACHPt-loaded Toroidal mixed micelles still could be witnessed their hollow regions and corona structures of the toroids.

Example 2. Internalization Behaviors in Static States

Since the introduced metal complex, DACHPt is a potent anti-colon cancer reagent, our primary assessments were carried out with a view towards biomedical application as a drug delivery system for cancer treatment. Among all nanoparticles applied as a drug delivery, the spherical nanoparticles are common. Herein, we encapsulated the DACHPt directly into the polymeric mixed micelles, comprising TPGS and PBLG. The DACHPt-loaded polymeric mixed micelles (DACHPt-loaded Spherical polymeric mixed micelles) were observed spherical using a TEM. The particle size determined by DLS was 294.6±19.7 nm and the ζ potential was −8.68±1.37 mV, which were approximated based on DACHPt-loaded toroidal mixed micelles. However, the Young's modulus of the DACHPt-loaded spherical polymeric mixed micelles, measured by atomic force microscope nano-indentation was 1.5-fold higher than DACHPt-loaded toroidal mixed micelles. That can account for that the DACHPt molecules mainly aggregate in the core of the spherical mixed micelles, while these molecules were distributed around the arms of the toroidal mixed micelles. The core-shell structures of DACHPt-loaded Spherical polymeric mixed micelles prevented themselves from intense particle increasing in water or phosphate buffering saline (PBS) upon time under shaking. In contract, the particles of DACHPt-loaded toroidal mixed micelles gradually increased upon time in $H_2O$ or PBS. Even though the increments in particles were detected, the drug releasing profiles of DACHPt-loaded toroidal mixed micelles displayed slow releasing curves in water and PBS conditions, approximating to that of DACHPt-loaded spherical polymeric mixed micelles did. The increments in particle sizes can ascribe to the transformation of the toroidal mixed micelles. Furthermore, the DACHPt-loaded spherical and toroidal mixed micelles were comparison for their in vitro behaviors as a drug delivery system.

Figure 5A:
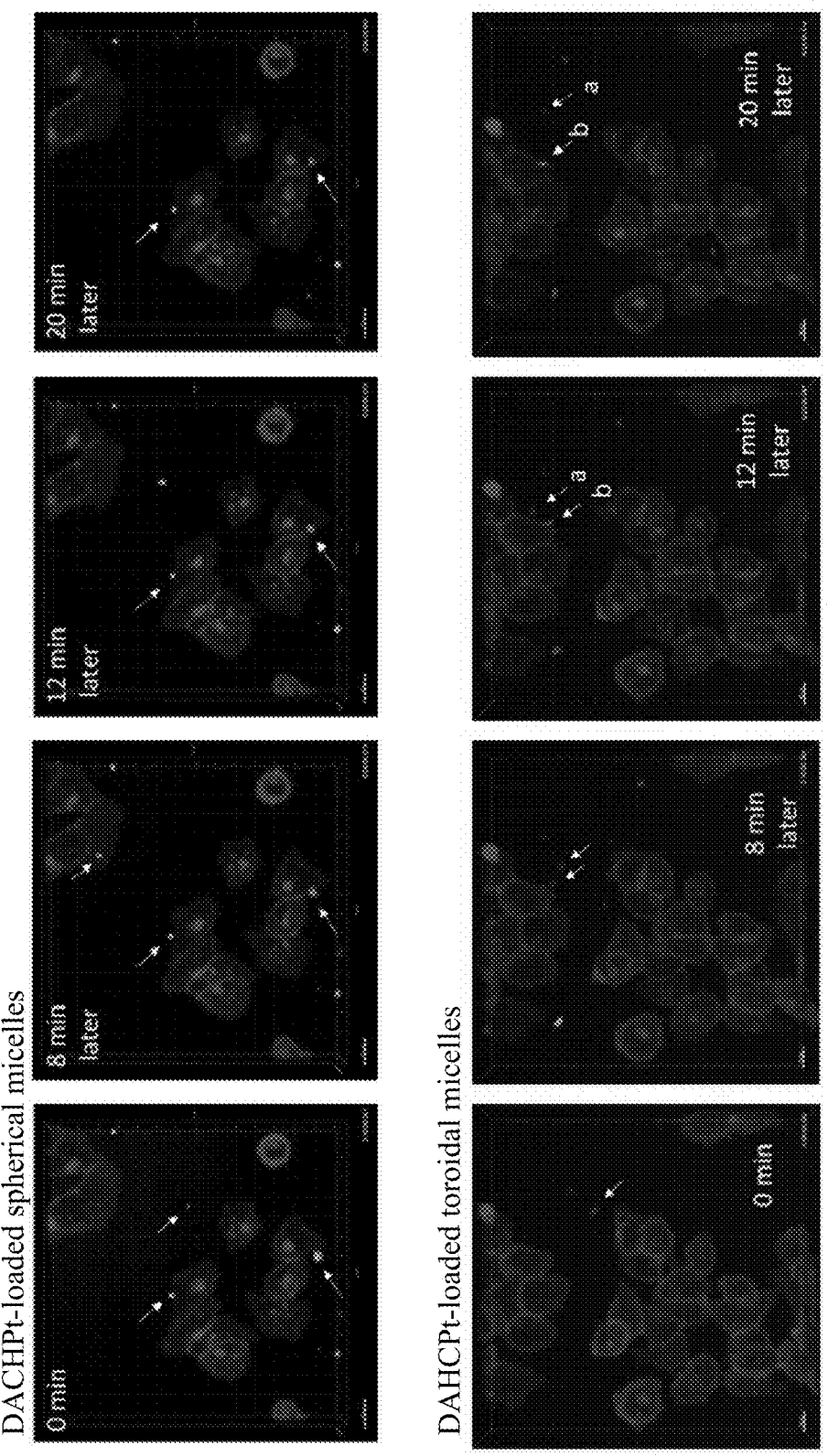

Since the platinum derivatives were potent to colorectal cancers in clinics, the toroidal mixed micelles of the present disclosure were aimed for the treatments of the colorectal cancers. Firstly, we investigated the interactions of DACHPt-loaded spherical and toroidal mixed micelles toward human colon cancer HCT116 cells in static state to mimetic DACHP-loaded micelles were transportation into tumor tissues. After conjugation on a fluorescent dye, 5/6-carboxyfluorescein succinimidyl ester (FITC-NHS ester) on the amine-functionalized spherical polymeric mixed micelles and toroidal mixed micelles by replacing the amine-derived TPGS, we independently incubated the FITC-labeled DACHPt-loaded spherical polymeric mixed micelles and toroidal mixed micelles with human colon cancer cell line HCT116 and their interactions were tracked using a real-time high-speed confocal laser scanning microscopic system (real-time high-speed CLSM system) for 1 h after staining the cell membrane. As FIG. 5A shows, the fluorescent toroidal micelles (presented in green) showed dynamic alterations in their shape or orientation during the period of incubation with HCT116 cells, due to the flexibility—like a rubber band. The rubber-band-like motions of FITC-labeled DACHPt-loaded toroidal mixed micelles influenced their orientations and contact surfaces with respect to colon cancer cells. As shown in FIG. 5A, when FITC-labeled DACHPt-loaded yoroidal mixed micelles attached to the cell membrane with the circular curvatures at the edges of the DACHPt-loaded toroidal mixed micelles, as schematically illustrated on left in FIG. 5B, they appeared as fluorescent dots (represented as "a" in FIG. 5A) on the cell membrane. Subsequently, they were not internalized into the cancer cells, and facilely detached from the cell membrane. However, when the coils of toroidal mixed micelles or the elongated toroidal mixed micelles integrated with the cell membranes, as schematically illustrated on right in FIG. 5B, whose shapes were observed as fluorescent rods (see "b" in FIG. 5A), FITC-labeled DACHPt-loaded toroidal mixed micelles tended to experience cellular binding and internalization. The contact orientation effects of DACHPt-loaded toroidal mixed micelles were observed and confirmed by SEM images, as shown in FIGS. 5C-1 and 5C-2. When the DACHPt-loaded toroidal mixed micelles adopted a spherical shape on the cellular membrane, as FIG. 5C-1 shows, internalization was not initiated; however, as the DACHPt-loaded toroidal mixed micelles displayed deformation or approached elongated coils, the particles were engulfed into the cells, as FIG. 5C-2 shows. This contact orientation effects of DACHPt-loaded toroidal mixed micelles can account for the association with the contact area and the attractive force. The DACHPt-loaded toroidal mixed micelles contact the cells with the circular curvatures at the edges, and they were observed to stand on the cell membrane at almost a single point; at the same time, their narrow contact surface led to minimal binding force. After temporary contact, DACHPt-loaded toroidal mixed micelles finally detached from the cells. Meanwhile, when the DACHPt-loaded toroidal mixed micelles contacted the cancer cells with the elongated coils, their contact area was much larger, and the driven force was substantial. Therefore, they were able to stay longer on the surfaces of cells and could be substantially internalized into the cells.

The contact orientation effect of the toroidal mixed micelles, which led from the flexibility and transformation can also explain the distinct endocytic pathways from those of the spherical mixed micelles. After the addition of methyl-β-cyclodextrin or incubation the cells in hypertonic sucrose in advance, the cells reduce the uptakes of the FITC-labeled DACHPt-loaded spherical polymeric mixed micelles; whilst, as the cells were pretreated with amiloride and hypertonic sucrose, the cells decreased the uptakes of DACHPt-loaded toroidal mixed micelles. The results demonstrate that both spherical and toroidal mixed micelles can be internalized into HCT116 cells via clathrin-dependent pathway. Besides, the spherical mixed micelles can also be internalized into other clathrin-dependent pathways, such as caveolae-dependent pathway; the toroidal mixed micelles can be internalized into HCT116 cells via macropinocytosis. The initiation of the macropinocytosis by the toroidal mixed micelles can be ascribed to the contact orientation effects. The toroidal mixed micelles must stretch and expand their contact surface to adhere onto the cells before uptaken by HCT116 cells.

The contact orientation effect of the toroidal mixed micelles significantly influenced the internalization into cancer cells. In comparison of the spherical mixed micelles, less DACHPt-loaded toroidal mixed micelles were uptaken into HCT116 cancer cells after incubation for a relatively long period (1, 3, and 6 h). For DACHPt-loaded toroidal mixed micelles, the contact orientation executed their initiation of the cell uptakes, while for DACHPt-loaded spherical polymeric mixed micelles, they almost can be internalized into cells upon they contacted to the cells. When the cells were incubated at 4° C. to hinder the endocytosis for 30 min, the HCT1116 cells internalized less mixed micelles. It is noticeable that the cells reduced approximately 50% of the DACHPt-loaded spherical polymeric mixed micelles uptakes, while the HCT116 cells only reduced 23.5% of the toroidal mixed micelles. This result clarifies that for the spherical mixed micelles, they can be rapidly adhesion onto the cells and uptakes, while for toroidal mixed micelles, their internalization mainly depends on the cell adhesion, due to their contact orientation effect.

Figure 5D:
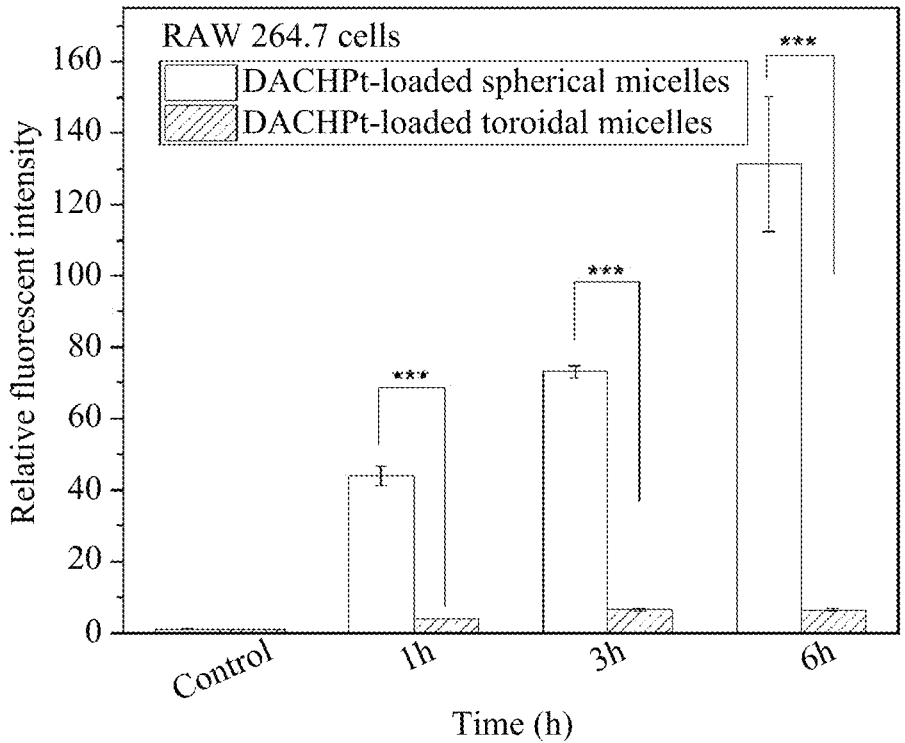
Figure 5E:
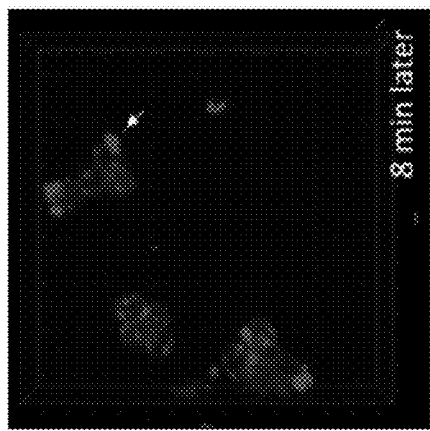
Figure 5E:
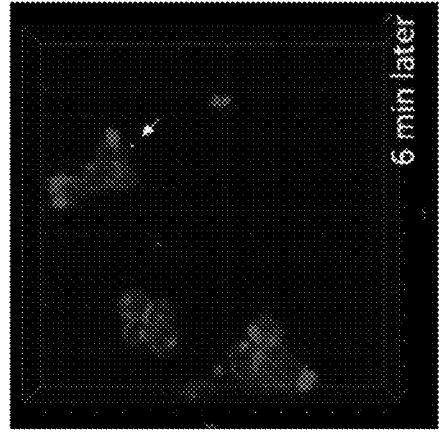
Figure 5E:
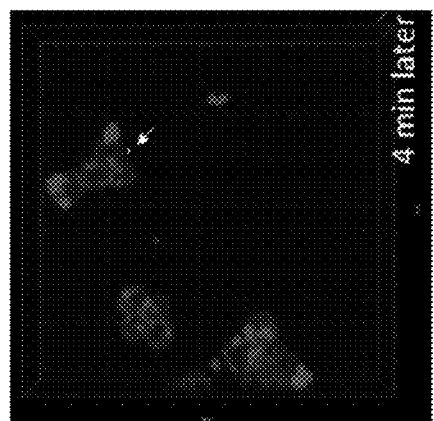
Figure 5E:
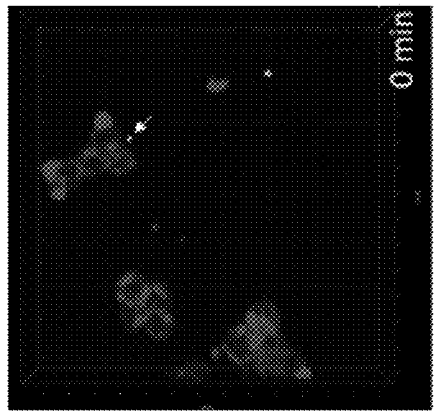

The contact orientation effect, originated from the flexibility and transformation of DACHPt-loaded toroidal mixed micelles was also observed when they were incubated with other cell lines, such as murine macrophage cell line RAW 264 (show in FIG. 5D). As shown in FIG. 5E, the macrophage cells vigorously internalized the spherical mixed micelles more than the toroidal ones. The lower uptakes into macrophage cells of DACHPt-loaded toroidal mixed micelles were due to the contact orientation effects. The contact orientation effects impeded those DACHPt-loaded toroidal mixed micelles, which attached to cells with one point at the edge, from being internalized, and therefore the total cell uptake upon incubation was reduced; whilst the DACHPt-loaded spherical polymeric mixed micelles would be adhere onto the macrophages and internalize upon incubation periods. Notably, the total uptakes into macrophage cells were higher than those into cancer cells. The macrophage cells internalized 10-fold more DACHPt-loaded spherical polymeric mixed micelles than the colon cancer cells did upon incubation periods, while the macrophage RAW 264.7 cells only internalized 2-fold more DACHPt-loaded toroidal mixed micelles than the colon cancer HCT116 cells did. The results imply that more spherical mixed micelles could be internalized into macrophage cells distributed in normal organs before they reached the tumor tissues, while toroidal mixed micelles were able to reduce the uptakes of the macrophages and hence enhance their tumor deposits.

Example 3. In Vitro Behaviors Under Flow Conditions

Figure 6A:
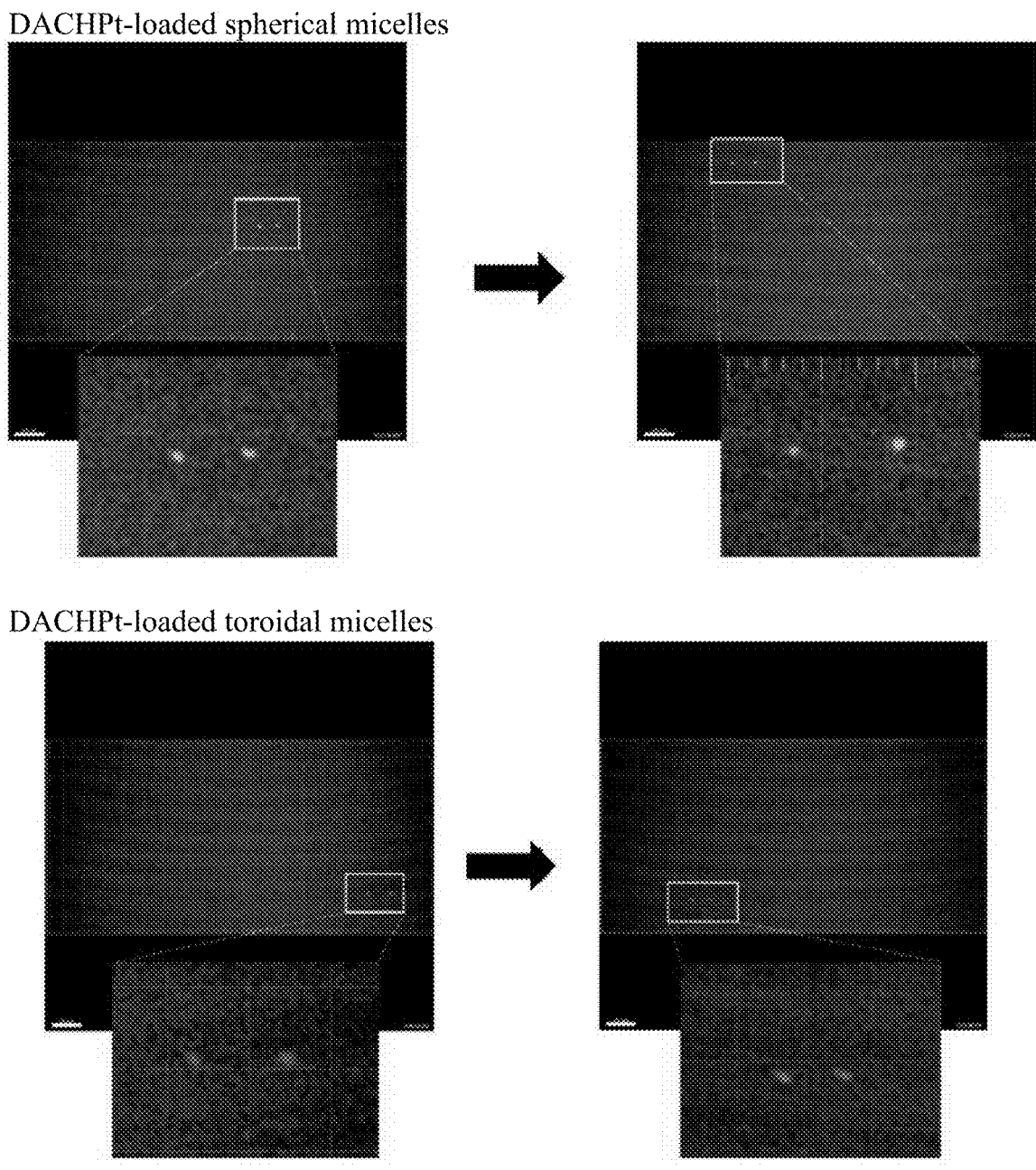
FIGS. 6A to 6D indicates in vitro behaviors under flow conditions. FITC-labeled DACHPt-loaded spherical polymeric and toroidal mixed micelles were passed through a microfluidic channel under 0.1 mL/min velocity (shown in FIG. 6A). The FITC-labeled DACHPt-loaded spherical polymeric mixed micelles toroidal mixed micelles were passing through 220 nm cutoff porous membranes with 0.1 mL/min flow rate for 30 min (shown in FIG. 6B). The extrusive fluorescence was measured. The FITC-labeled DACHPt-loaded polymeric spherical and toroidal mixed micelles (shown in bright green indicated by the white arrow) were steadily injected under 0.1 mL/min velocity into a 50-mm-long, 5-mm-wide and 200-μm-high channel, where the murine macrophage cells RAW 264.7 were seeded and attached in advance (shown in FIG. 6C). The cell adhesion of the FITC-labeled DACHPt-loaded spherical polymeric mixed micelles and toroidal mixed micelles under 0.1 mL/min velocity passing through a channel where were seeded RAW 264.7 cells for 30 min (shown in FIG. 6D). The FITC fluorescence of the adhesive micelles were determined using a flow cytometry.
Figure 6B:
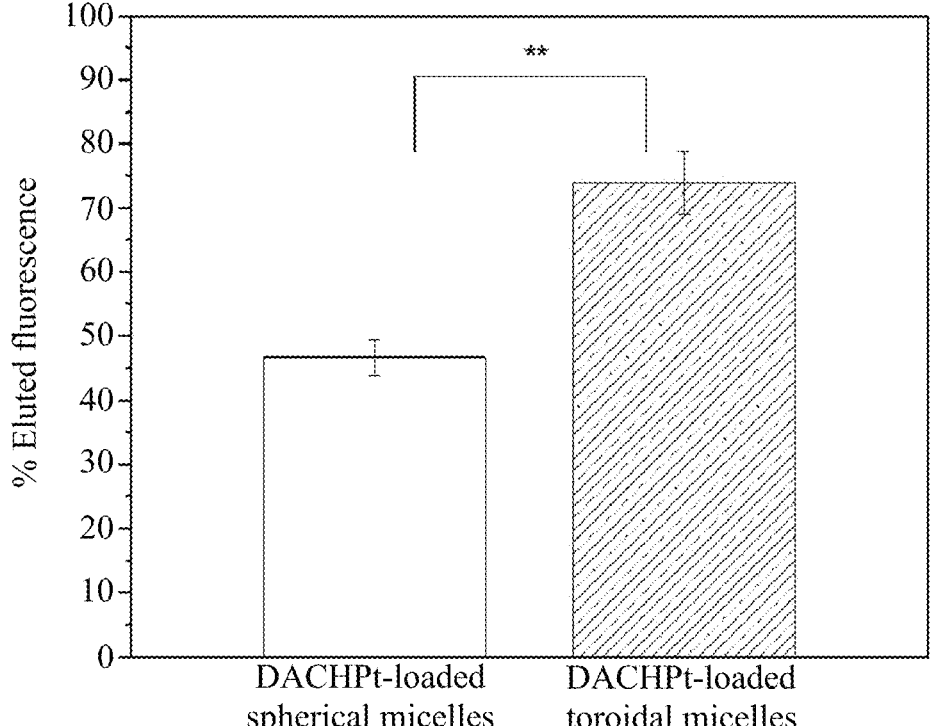

In authentic human physiology, before entry into solid tumor tissues, the mixed micelles were transported in the blood vessels and the most importantly, under flow conditions. Herein, the behaviors of DACHPt-loaded toroidal mixed micelles were investigated and compared to the spherical mixed micelles under flows. Firstly, the real-time morphology of these FITC-labeled mixed micelles was observed using a high-speed laser scanning microscopy in a microfluidic channel under 0.1 mL/min of velocity, which was considered laminar flow conditions to mimetic their transportation in the blood. FITC-labeled DACHPt-loaded spherical polymeric mixed micelles displayed a dot-like shape with subtle deformation under flow conditions. However, DACHPt-loaded toroidal mixed micelles showed a dynamic transformation in the microfluidic channel, as shown in FIG. 6A. The DACHPt-loaded toroidal mixed micelles were observed dynamically transform from a dot-shaped to an elongated nanoparticle under laminar flows. This dynamic motion can be attributed to the flexibility of the toroidal mixed micelles and their spinning and tumbling effects under flow conditions. In addition, the superb flexibility and dynamic transformation of the toroidal mixed micelles led to higher extrusive efficacy as they passed through smaller porous membranes (220 nm cut-off) under flow conditions, as FIG. 6B shows. As mentioned above, the particle sizes of the spherical and toroidal mixed micelles were approximately 300 nm. However, FIG. 6B shows that only 46.7% of the spherical mixed micelles enable to be extrusion through the membrane at the rate of 0.1 mL/min, while 1.5-fold more toroidal mixed micelles can pass through the same sizes of the porous membrane, due to their flexibility. These results suggest that the toroidal mixed micelles had more chances to pass through small pores under flows, such as the leakage of the angiogenesis blood vessels from the laminar blood.

Figure 6C:
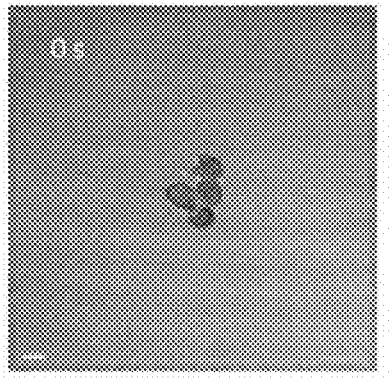
Figure 6C:
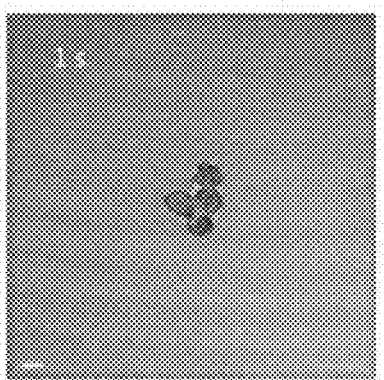
Figure 6C:
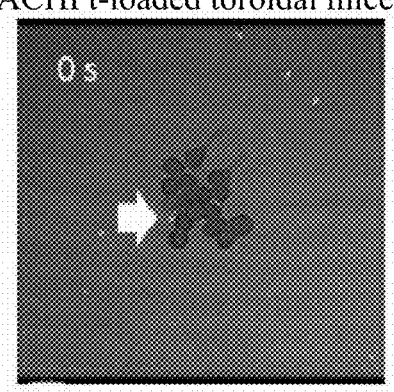
Figure 6C:
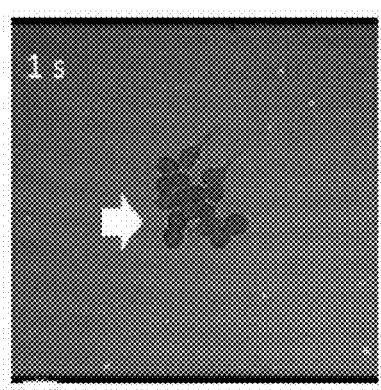
Figure 6C:
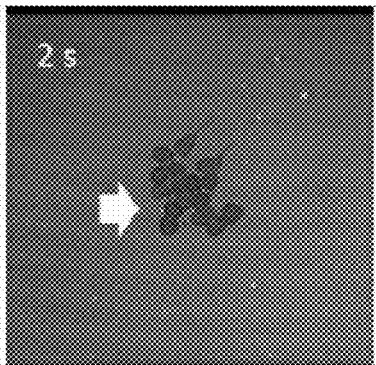
Figure 6C:
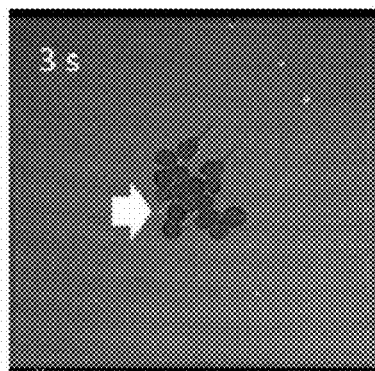
Figure 6C:
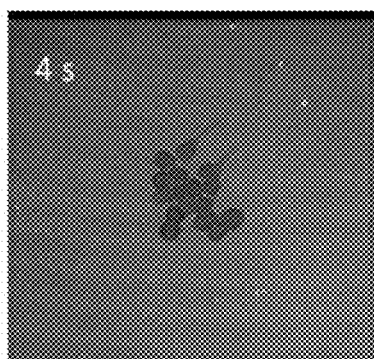
Figure 6D:
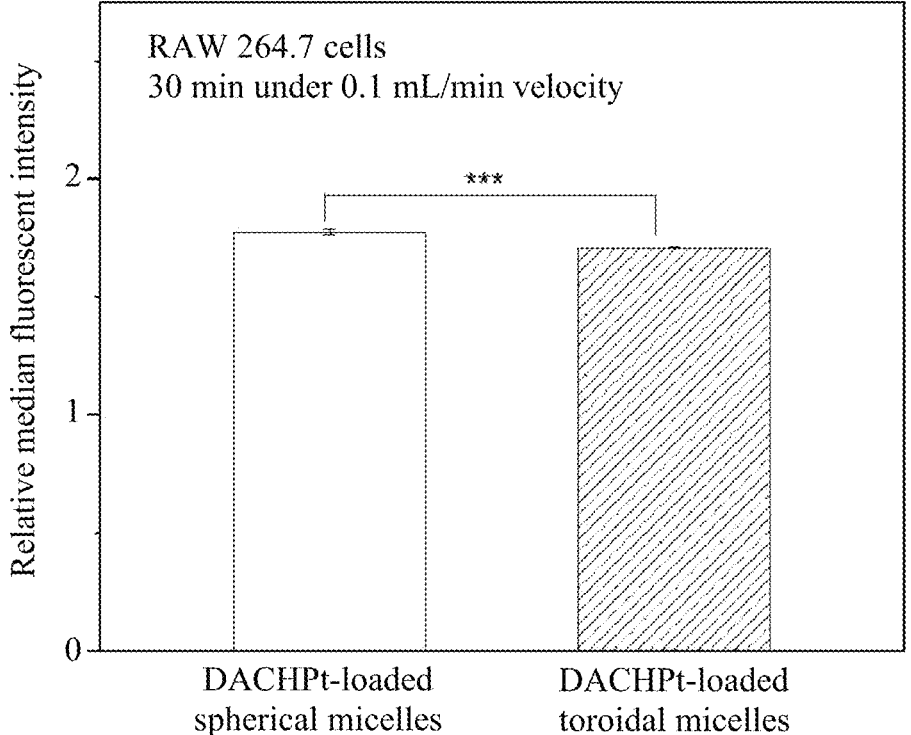

Furthermore, we investigated the interactions of the mixed micelles and the macrophage cells under flow conditions to mimetic the mixed micelles transportation and flow by the macrophage-enriched organs. The murine macrophage cells RAW 264.7 were seeded in the channel of 5 mm in width and 200 μm in height on the chip and afterwards, FITC-labeled DACHPt-loaded spherical polymeric mixed micelles and toroidal mixed micelles passed through the channel and cells under 0.1 mL/min velocity, where the flows were identified laminar after calculation. Firstly, the interactions between mixed micelles and cells were observed with a high-speed laser microscopy, as FIG. 6C shows, the DAHCPt-loaded TM underwent a dynamic transformation upon time and subsequently was far away from the cells. However, 30 min later, in comparison to the DACHPt-loaded spherical polymeric mixed micelles, 5% of DACHPt-loaded toroidal mixed micelles were reduction in avoidance of the macrophage uptakes under flow conditions, as FIG. 6D shows. These results implied that DACHPt-loaded toroidal mixed micelles have ability to escape from the resident macrophage in organs during blood transportation.

Example 4. In Vitro Tumor Penetration Behaviors

Figure 7A:
FIGS. 7A to 7C reveal penetration into human colon cancer cell HCT116 spheroids in static state. The human colon cancer cell line HCT116 was incubated onto a bioinert dish. At 3 d post-incubation, the cells were incubated with FITC-labeled DACHPt-polymeric spherical and loaded toroidal mixed micelles (shown in bright green indicated by the white arrow) (shown in FIGS. 7A and 7B). The cell spheroids and the fluorescence of the mixed micelles were observed using a confocal laser scanning microscopic (CLSM) system. DACHPt-loaded toroidal mixed micelles contact with a dot-like (shown in FIG. 7A) or elongated shapes (shown in FIG. 7B) were observed. The tumor penetration was also evaluated over time using the Incucyte® live-cell analysis systems. FITC-labeled DACHPt-loaded toroidal mixed micelles were incubated with the HCT116 tumor spheroids, which have been stained with cell tracking fluorescent dyes (shown in FIG. 7C).
Figure 7A:
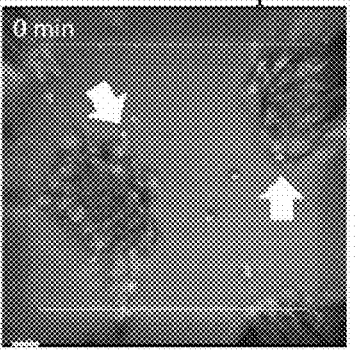
Figure 7A:
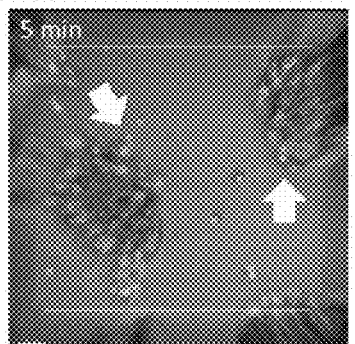
Figure 7A:
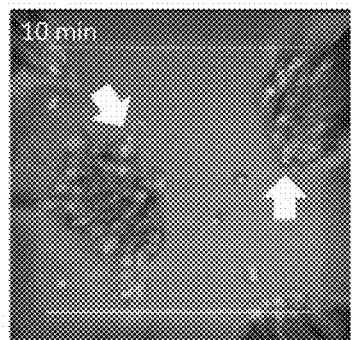
Figure 7A:
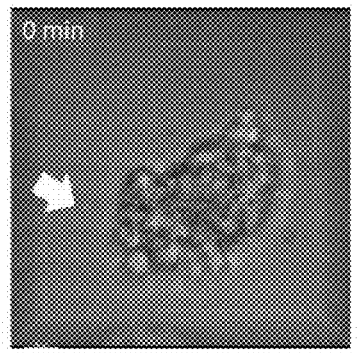
Figure 7A:
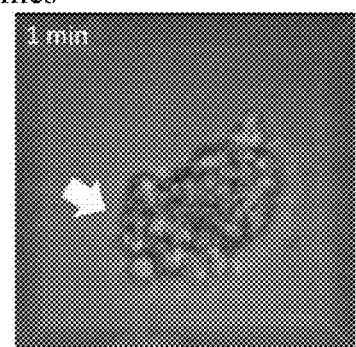
Figure 7A:
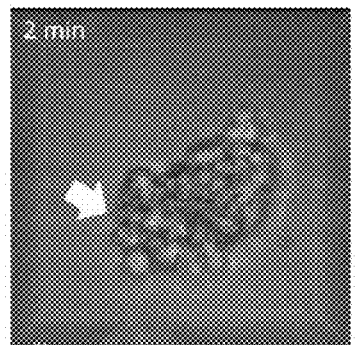
Figure 7B:
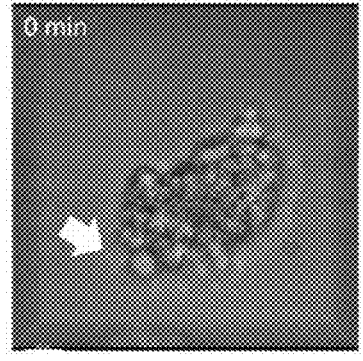
Figure 7B:
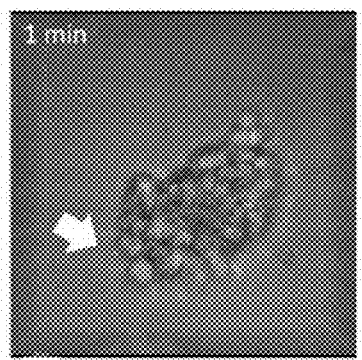
Figure 7B:
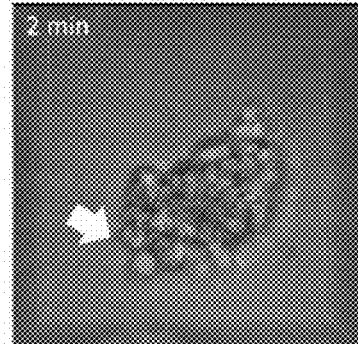
Figure 7C:
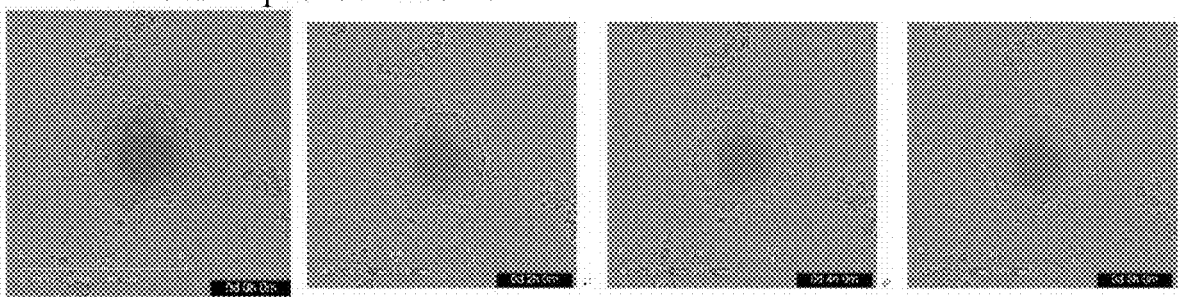
Figure 7C:
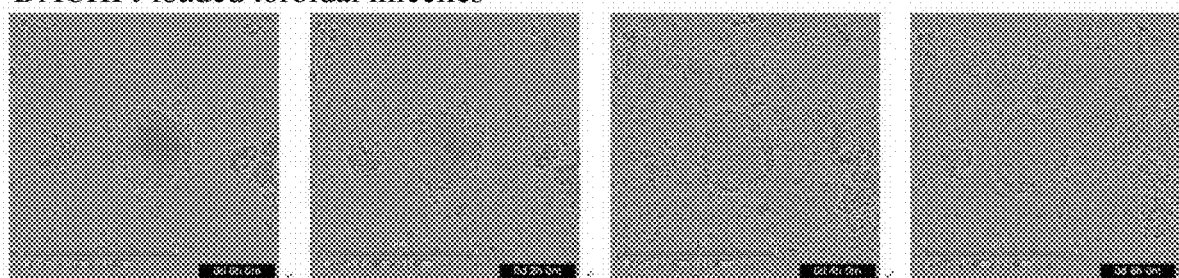

As the mixed micelles extravasate from blood vessel leakage and arrive at tumor lesions, the tumor penetration become another issue for drug delivery. Herein, the effects to 3D tumor penetration was investigated. Firstly, the human colon cancer HCT116 cells were seeded onto the bioinert dishes, forming 3-dimensional (3D) tumor spheroids. The FITC-labeled spherical and toroidal mixed micelles thereby were applied and their behaviors were respectively observed via a high-speed confocal laser scanning microscopy and recorded as FIGS. 7A to 7C shows. The DACHPt-loaded spherical polymeric mixed micelles attached to the outer cells and were impeded from penetration due to the closely packing and small gaps of the cells. However, as FIGS. 7A and 7B show, the DACHPt-loaded toroidal mixed micelles displayed two performances upon their contact orientation. As FIG. 7A indicates, when the DACHPt-loaded toroidal mixed micelles contacted to superficial cell spheroids with tiny surface, the micelles could directly pass through the cellular gaps; however, as FIG. 7B presents, when the DACHPt-loaded toroidal mixed micelles contacted to the superficial cells of the spheroid with their pan or elongated surface, they adhered to the cell surface and slowly internalized into the cells. This result again verified the significance of the transformation and the contact orientation effect for the toroidal mixed micelles.

The tumor penetration was also monitored upon incubation periods and the images were present in FIG. 7C. The FITC-labeled DACHPt-loaded micelles (present in green) were treated with the fluorescence-labeled human colon cancer cell HCT116 spheroids (present in red). In FIG. 7C, the green fluorescence, representing the DACHPt-loaded toroidal mixed micelles was observed gradually overlapped the red fluorescence of the cells. After 6 h incubation, most area of the tumor spheroids were even occupied by the green fluorescence. The results clearly demonstrate that the toroidal mixed micelles had better efficacy in tumor penetration than the spherical mixed micelles did. That attributed to that the toroidal mixed micelles enabled to deform and cross the tight cell-cell voids within the spheroids.

Example 5. In Vivo Tumor Accumulation and Biodistribution

Figure 8A:
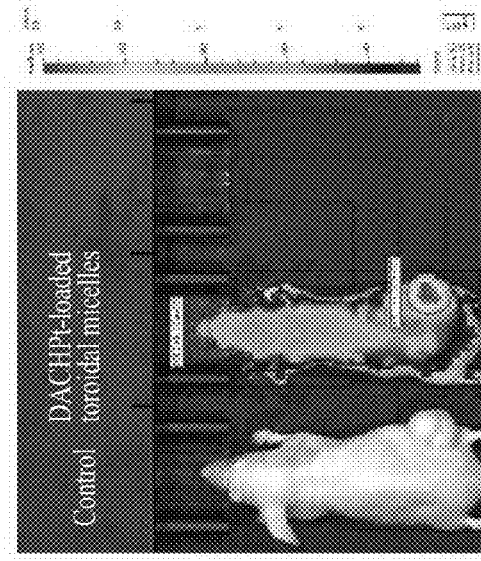
FIGS. 8A to 8E indicates in vivo optical fluorescent images of HCT116-cell-inoculated nude mice after 24 h i.v. injection with Cyanine 5.5-labeled DACHPt-loaded polymeric spherical and mixed micelles. The colors represent the fluorescent intensities of accumulation in mice and in organs after 24 h i.v. administration with Cyanine 5.5-labeled DACHPt-loaded toroidal mixed micelles (shown in FIG. 8A). Region of interest (ROI) ratio was determined by the fluorescence intensity in tumor over that in whole body (shown in FIG. 8B). The biodistribution of Cyanine 5.5-labeled DACHPt-loaded spherical polymeric and toroidal mixed micelles in the HCT116 human colon cancer cell xenografted Balb-c/nude mice after 24 h of intravenous injection (shown in FIG. 8C). The penetration through the blood vessels of Cyanine 5.5-labeled DACHPt-loaded polymeric spherical and toroidal mixed micelles was observation using a confocal system (shown in FIG. 8D). The blood vessels were stained and their fluorescence were present in green. The fluorescence Cyanine 5.5 represent in red and the cell nuclei were present in blue. The observation of the liver macrophage uptakes of Cyanine 5.5-labeled DACHPt-loaded polymeric spherical and toroidal mixed micelles (shown in FIG. 8E). The macrophages were stained and their fluorescence was present in green; the fluorescence o Cyanine 5.5 and the cell nuclei were respectively present in red and blue.
Figure 8A:
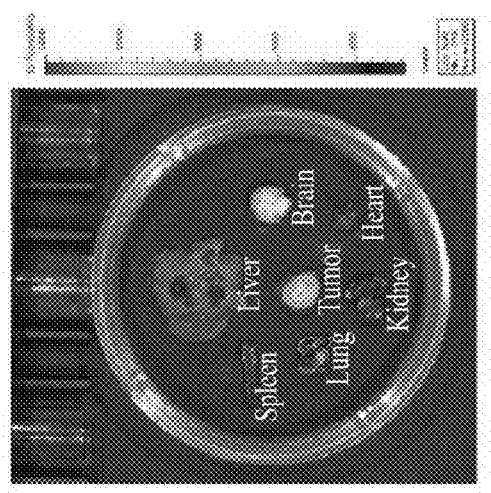
Figure 8A:
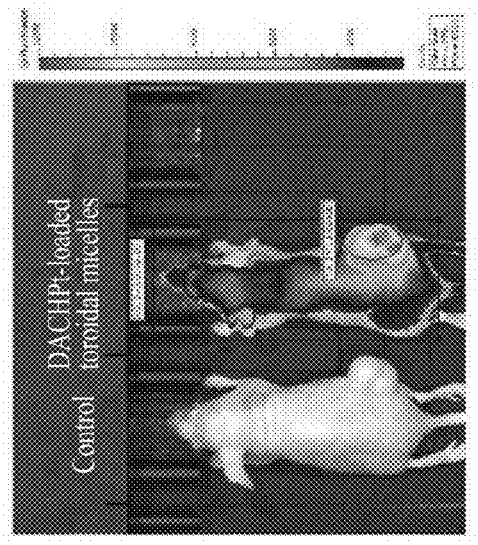
Figure 8A:
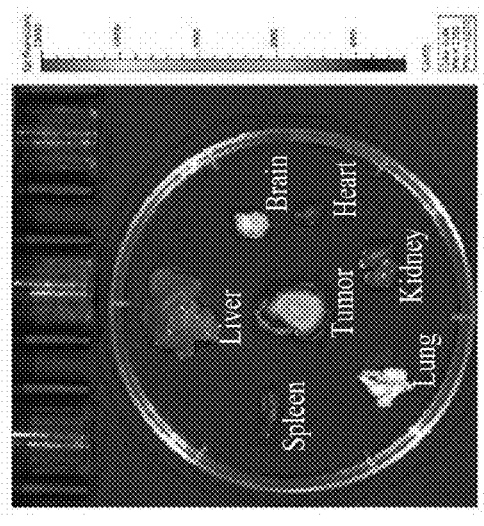
Figure 8A:
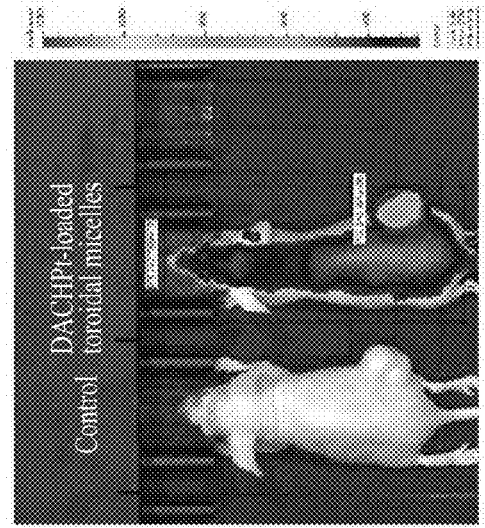
Figure 8A:
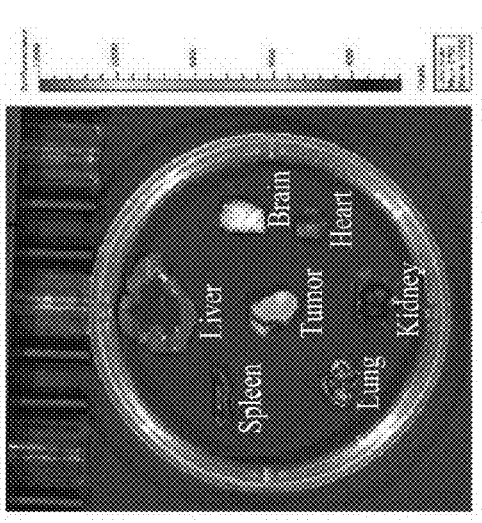
Figure 8B:
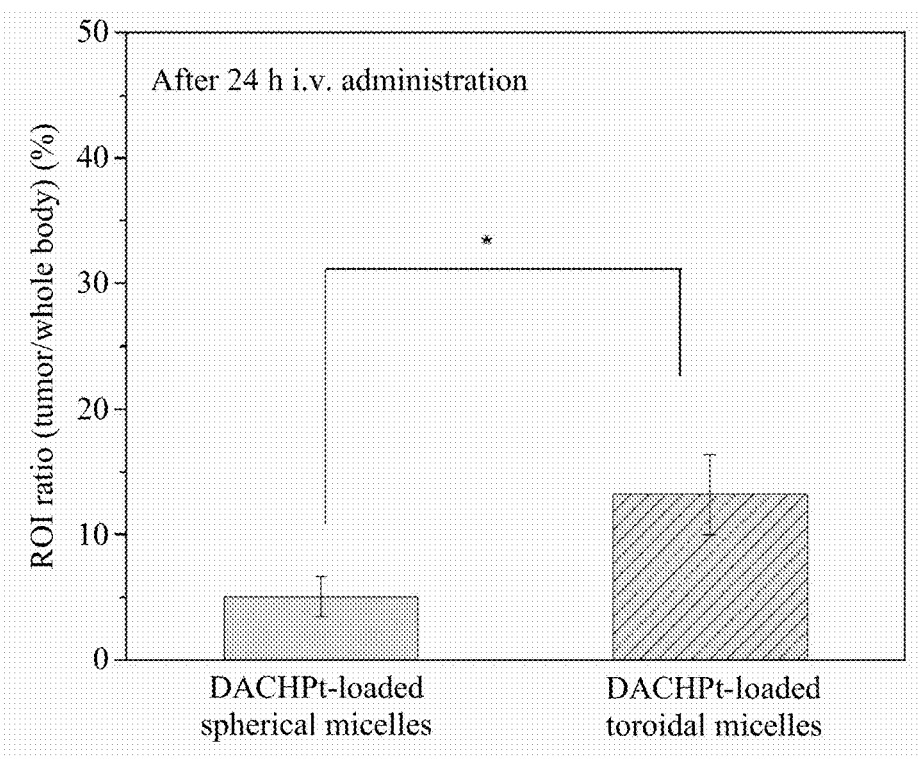
Figure 8C:
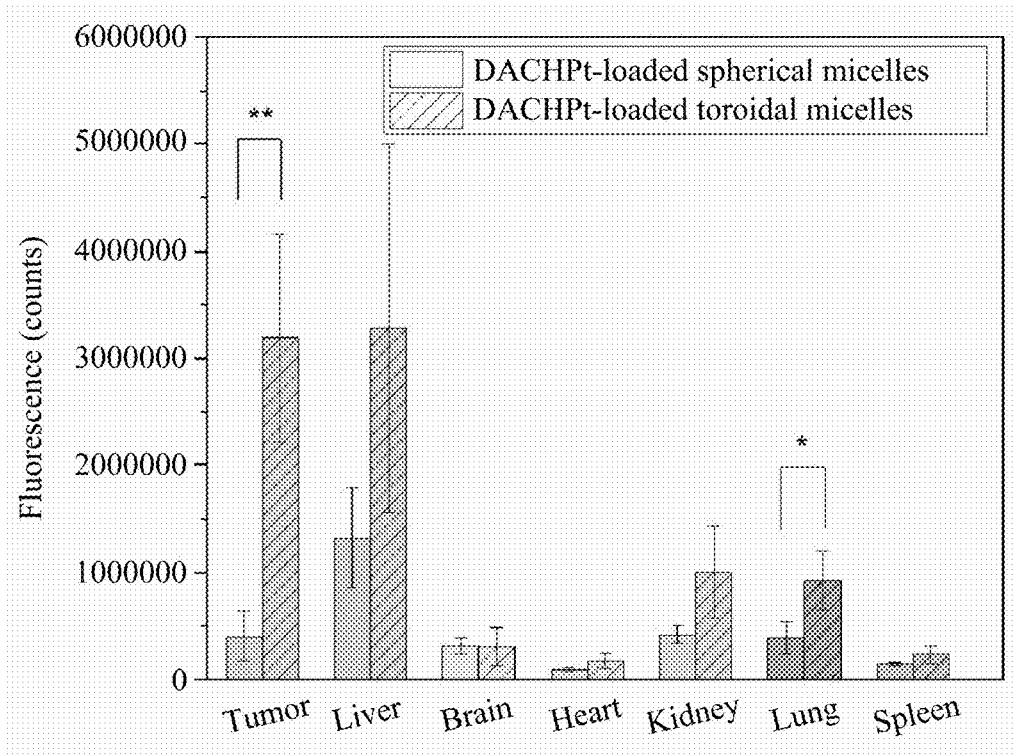
Figure 8D:
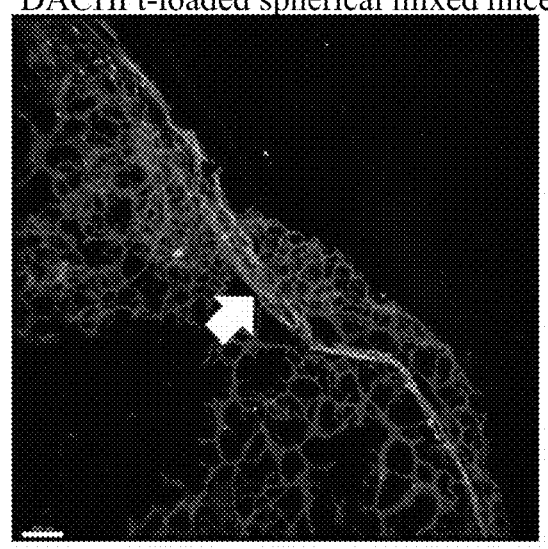
Figure 8D:
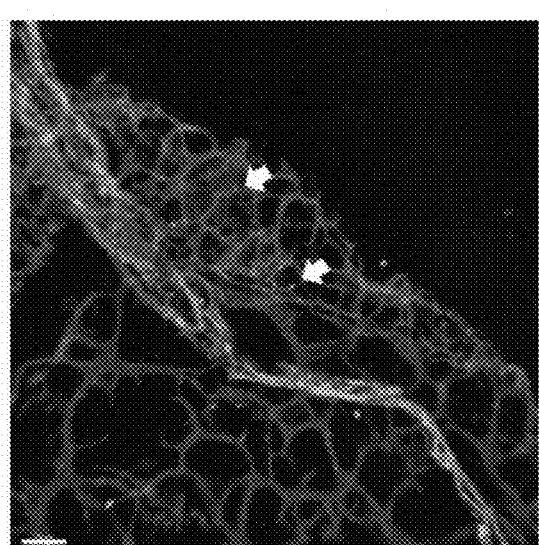
Figure 8D:
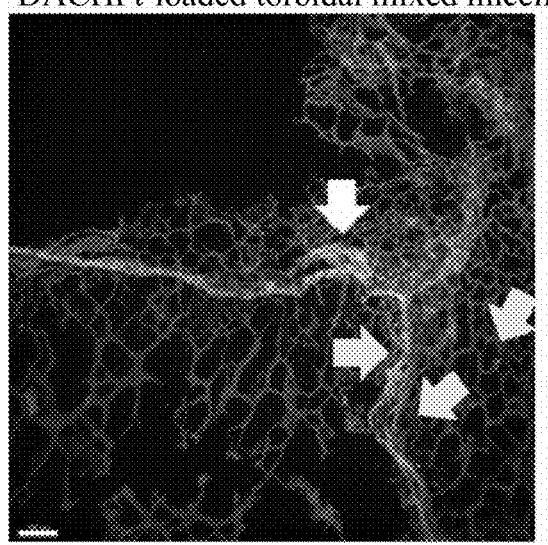
Figure 8D:
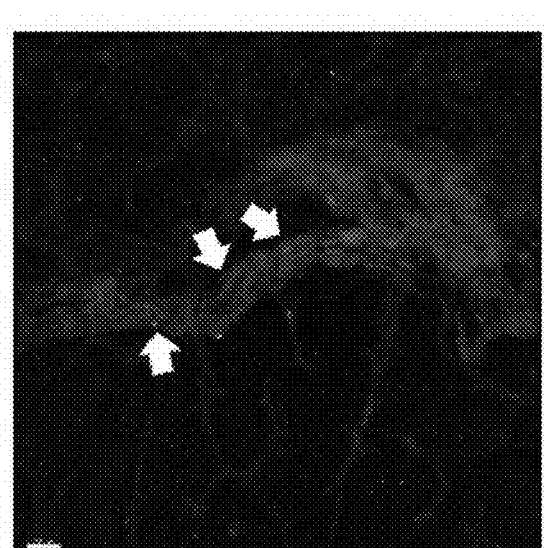

On the basis of the in vitro studies of the DACHPt-loaded toroidal mixed micelles, the DACHPt-loaded toroidal mixed micelles have an exceptional ability when it comes to extravasation from blood vessel, tumor penetration and low cell uptake into macrophages in either static state or flow conditions. Furthermore, the biodistribution and tissue deposits were first explored for the DACHPt-loaded toroidal mixed micelles, in comparison of those for the DACHPt-loaded spherical mixed micelles to verify the in vitro properties. After labeling with the fluorescent dye Cy 5.5-NHS ester, following the same process as that described above for labeling FITC, Cy 5.5-labeled DACHPt-loaded spherical polymeric mixed micelles and toroidal mixed micelles were respectively intravenously (i.v.) administered into human colon cancer cell HCT116-xenografted mice. At 24 h post-injection, the fluorescence in mice was optically observed using an in vivo imaging system (IVIS), as shown in FIG. 8A. The images displayed for DACHPt-loaded spherical polymeric mixed micelles, intense fluorescence in tumors, illustrating that the tumor was the major accumulating site of DACHPt-loaded and toroidal mixed micelles (FIG. 8A.). However, as FIG. 8B indicates, the accumulation ratio in the tumor of DACHPt-loaded toroidal mixed micelles were approximately 2-fold higher than that of DACHPt-loaded spherical polymeric mixed micelles, because tumor was not the only major accumulating sites for DACHPt-loaded spherical polymeric mixed micelles. It is noticeable that for DACHPt-loaded spherical polymeric mixed micelles, intense fluorescence was also detected in liver, demonstrating that liver was also another major accumulating sites of DACHPt-loaded spherical polymeric mixed micelles. As FIG. 8C shows, for DACHPt-loaded spherical polymeric mixed micelles, the fluorescence in liver was even higher than that in tumors, while for DACHPT-loaded toroidal mixed micelles, the accumulation ratios in the tumor were much higher than those in other organs, including the kidneys, spleen, heart, and brain, as well the liver and lungs—organs associated with the reticuloendothelial system (RES). This high tumor accumulating tendency of DACHPt-loaded toroidal mixed micelles accounted for the flexibility. As FIG. 8D shows, DACHPt-loaded toroidal mixed micelles (shown in red) extravasated from the blood vessels (shown in green) with either larger-size gaps of the blood vessels or small leakages, performing their tumor-favorable tendency.

Figure 8E:
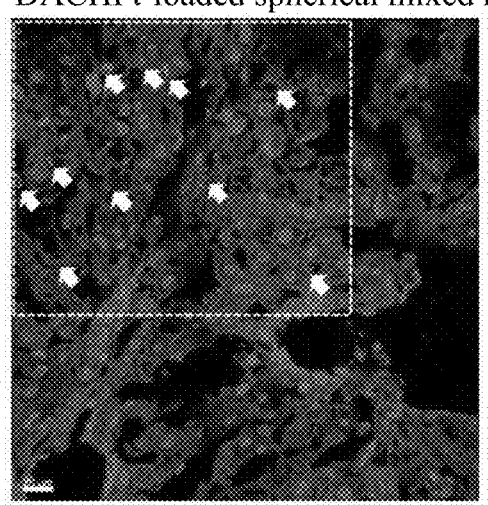
Figure 8E:
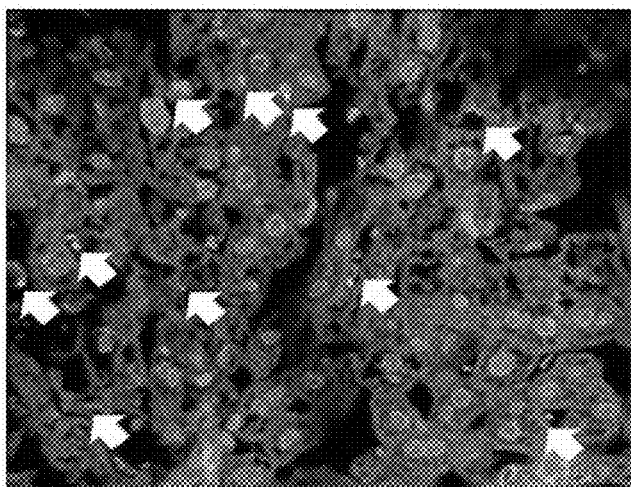
Figure 8E:
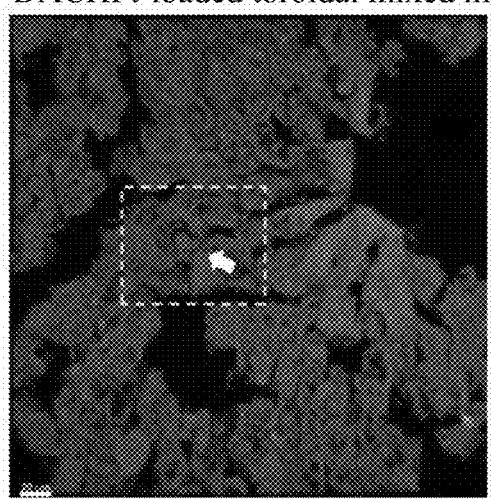
Figure 8E:
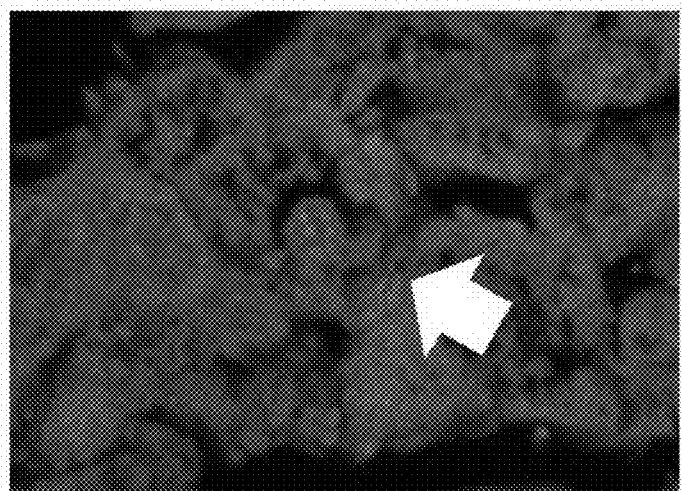

In addition, we also investigated the accumulation of DACHPt-loaded spherical and toroidal mixed micelles in liver, where asserted abundant macrophage cells after 24 h i.v. administration. The macrophage cells in liver were recognized with CD45 antibody and shown in green in FIG. 8E. As FIG. 8E shows, more DACHPt-loaded spherical polymeric mixed micelles were discovered in liver than DACHPt-loaded toroidal mixed micelles (indicated by white arrows) were. It is noticeable that the red fluorescence of DACHPt-loaded spherical polymeric mixed micelles was observed almost overlapping with the green fluorescence of macrophage cells, whereas the red fluorescence of DACHPt-loaded toroidal mixed micelles were witnessed locate neighboring the macrophage cells in FIG. 8E. The results can account for the contact orientation effect of the toroidal mixed micelles. The contact orientation effect retards the toroidal mixed micelles internalization into macrophage cells, therefore the toroidal mixed micelles returning back to the blood circulation. In summary, the results of tumor accumulation and biodistribution identify the in vitro properties of the toroidal mixed micelles and further suggest that the toroidal mixed micelles potentiate as a novel drug delivery system.

TABLE 2

Hepatic and renal functions after 16 d independently treatment with PBS (control), DACHPt molecules and DACHPt-loaded toroidal mixed micelles.

| | biomedical marker | | | |
| | hepatic functional index | | renal functional index | |
| code | AST (U/L) | ALT (U/L) | BUN (mg/dL) | Creatinine (mg/dL) |
| --- | --- | --- | --- | --- |
| Control | 442 ± 21 | 94 ± 19 | 36.1 ± 2.5 | 0.28 ± 0.02 |
| DACHPt | 134 ± 29 | 40 ± 3 | 32.9 ± 9.3 | 0.44 ± 0.05 |
| DACHPt-loaded TMs | 143 ± 36 | 42 ± 7 | 26.2 ± 6.5 | 0.44 ± 0.11 |

Example 6. In Vivo Anticancer Assessment

Figure 9:
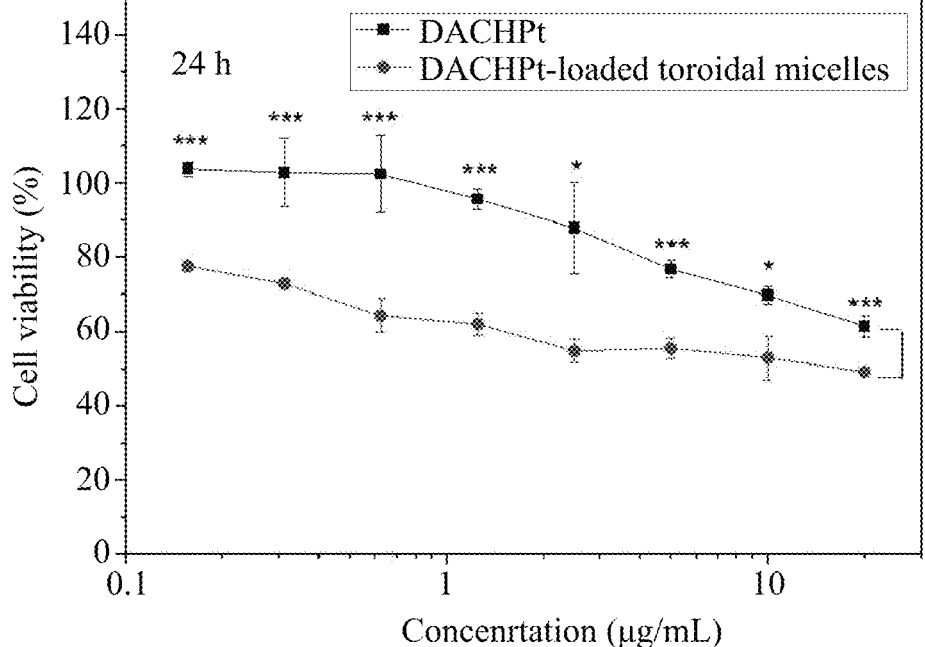
FIG. 9 shows cytotoxicity of DACHPt and DACHPt-loaded toroidal mixed micelles toward HCT116 human colon cancer cells. The cytotoxic effects were determined by an MTT assay. Error bars are the mean±S.D. of biological triplicates.
Figure 10:
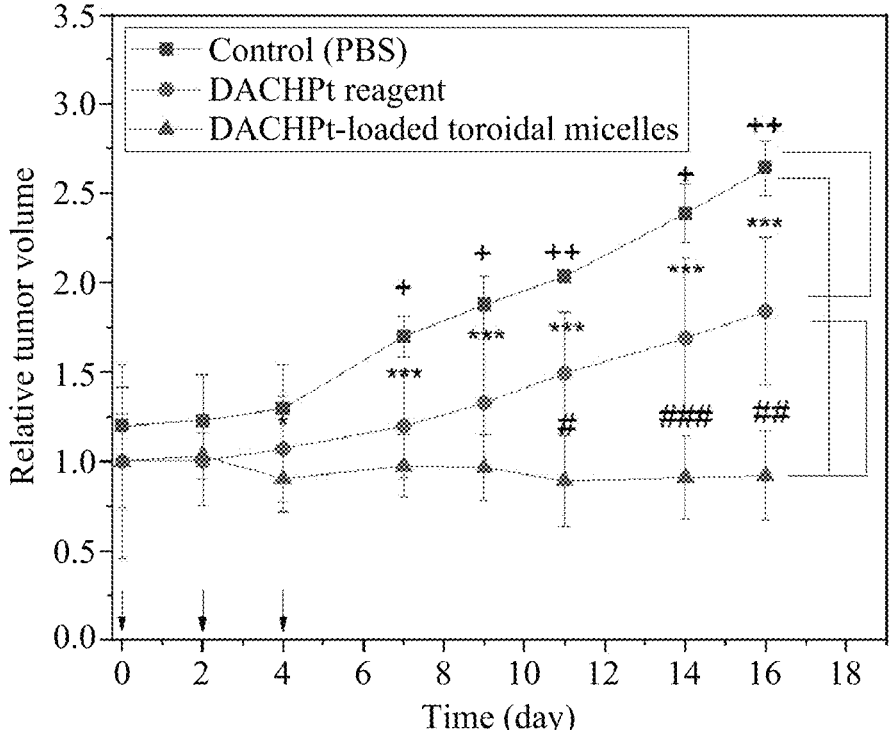
FIG. 10 shows in vivo antitumor tests. Tumor growth inhibition in Balb-c/nude mice xenografted with HCT116 human colon cancer cells after being intravenously administered PBS, DACHPt molecules, and DACHPt-loaded toroidal mixed micelles at days 0, 2, and 4. The results were statistically analyzed; significant differences are shown with asterisks (*, p<0.05; , p<0.01; and *, p<0.001).
Figure 11:
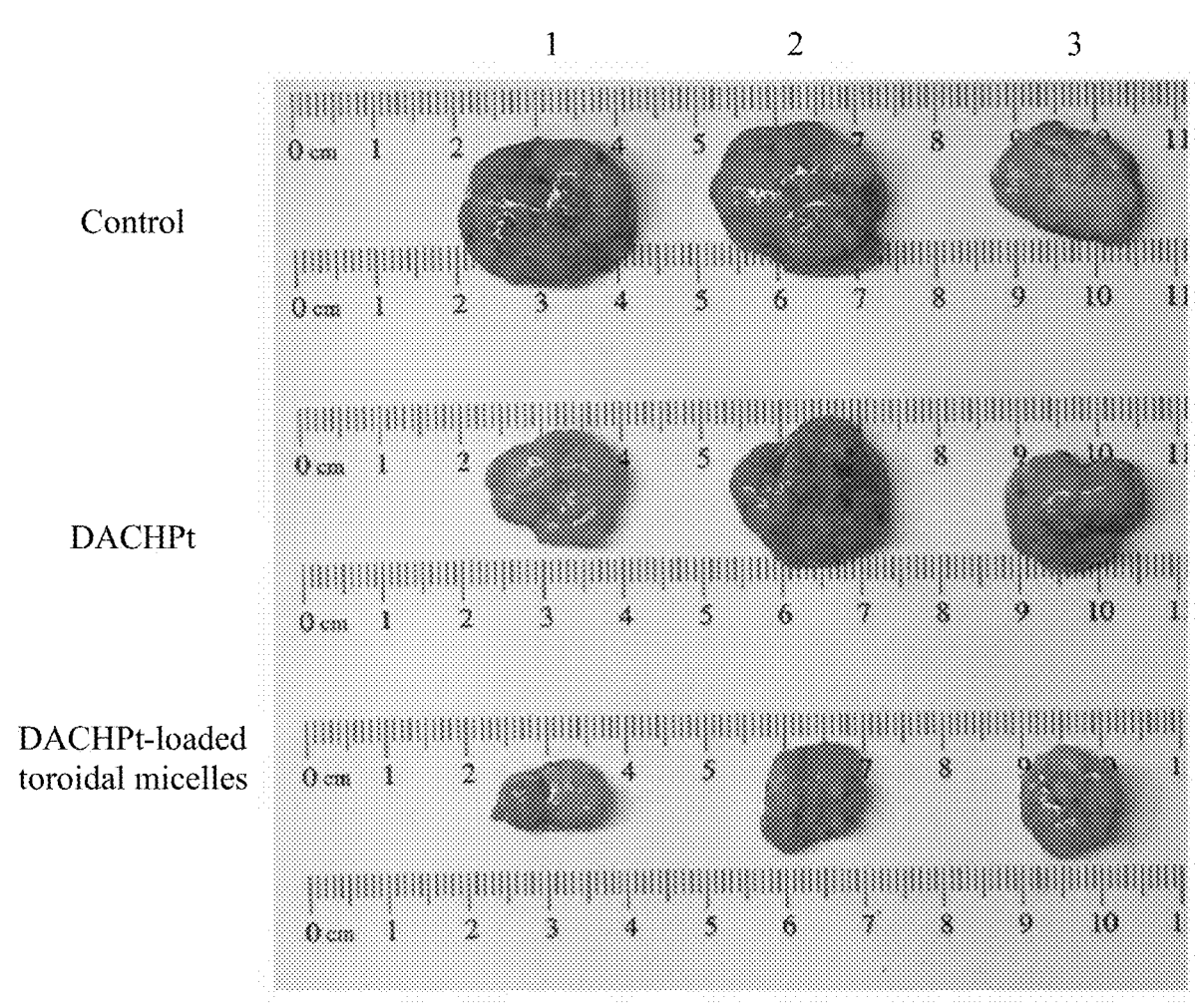
FIG. 11 shows the tumor growth of the DACHPt-loaded toroidal mixed micelles at Day 16 post-treatment. At Day 16 post-treatment, the human colon cancer cells HCT116 bearing mice were euthanasia and tumor tissues were collected. After exclusion the extreme sizes of the tumors, the other tumor tissues were photographed.

On the basis of the in vitro observation, partial DACHPt-loaded toroidal mixed micelles were not rapidly internalized into the cancer cells due to their contact orientation effects. Even though, DACHPt-loaded toroidal mixed micelles still caused considerable in vitro cell death in comparison with DACHPt molecules, as shown in FIG. 9. Besides, the toroidal mixed micelles have tremendous tumor accumulating ability in tumor-bearing mice. Furthermore, the in vivo antitumor efficacy of DACHPt-loaded toroidal mixed micelles as a platinum-derivative drug delivery system was evaluated in HCT116-cell-inoculated nude mice, as shown in FIG. 8A. The HCT116-cell-inoculated nude mice were independently given PBS (control), DACHPt molecules, and DACHPt-loaded toroidal mixed micelles at an adjusted dosage of 4 mg/kg based on the DACHPt concentration at days 0, 2, and 4. The result in FIG. 10 indicates that DACHPt-loaded toroidal mixed micelles shows exceptional antitumor efficacy. The tumor volumes of mice administered with DACHPt-loaded toroidal mixed micelles were reduced 16 d later, as shown in FIG. 11. At Day 16, the mice were euthanized, and their tumor/organs and blood samples were collected to analyze the toxicity after long-term treatment. The tumor H&E staining sections from the mice in the all groups were used to visualize the round to spindle tumor cells undergoing mitosis. The hematoxylin and eosin (H&E) staining sections further indicates that the livers, lungs, and spleens harvested from the mice in the control group were discovered to have multifocal tumor metastasis derived from the colon cancer cells, while the tumor metastasis only observed in lungs harvested from the mice treated with DACHPt molecules and DACHPt-loaded toroidal mixed micelles. The tumor metastasis in liver from the mice in the control groups led to abnormally increasing AST (aspartate transaminase) and ALT (alanine transaminase) values, which was assessed the hepatic functions in clinics, as shown in Table 2. The mice in the control groups treated only with PBS were found to have tremendous increases in their AST and ALT values, with values of 442±21 and 94±19 U/L, respectively—much higher than those of the mice, given that the contents of DACHPt molecules and DACHPt-loaded toroidal mixed micelles. Furthermore, the tumor harvested from the mice was analyzed the necrosis indexes, which was inversely association with the prognosis performance. The tumor harvested from the mice in the treatment of DACHPt-loaded toroidal mixed micelles displayed the lowest tumor necrosis scores. That can account for that DACHPt-loaded toroidal mixed micelles can efficiently accumulate into the tumor and inhibit the progression of those malignant cancer cells. These tests show that DACHPt-loaded toroidal mixed micelles displayed superior antitumor efficiency, low cytotoxicity and exceptional prognosis performance, clearly identifying their feasibility as a drug delivery system in anticancer therapy.

What is claimed is:

1. A toroidal mixed nanoparticle, comprising:
a first polymer; and
a second polymer interacting with the first polymer;
wherein the first polymer is an amphiphilic polymer, and the second polymer is a hydrophobic polymer; and
wherein the first polymer is d-α-tocopherol polyethylene glycol succinate, and the second polymer is a poly-γ-benzyl-1-glutamate.

2. The toroidal mixed nanoparticle of claim 1, being a toroidal mixed micelle.

3. The toroidal mixed nanoparticle of claim 1, having a diameter of from about 50 nm to about 1200 nm.

4. The toroidal mixed nanoparticle of claim 1, conjugated with a drug or a bioactive agent.

5. The toroidal mixed nanoparticle of claim 4, wherein the drug or the bioactive agent is selected from the group consisting of platinum derivatives, camptothecin, doxorubicin, methotrexate, 17-(Allylamino)-17demethoxygeldanamycin (17-AAG), celecoxib, capecitabine, docetaxel, epothilone B, Erlotinib, Etoposide, GDC0941, Gefitinib, Geldanamycin, Imatinib, Intedanib, lapatinib, Neratinib, NVP-AUY922, NVP-BEZ235, Panobinostat, Pazopanib, Ruxolitinib, Saracatinib, Selumetinib, Sorafenib, Sunitinib, Tandutinib, Temsirolimus, Tipifarnib, Tivozanib, Topotecan, Tozasertib, Vandetanib, Vatalanib, Vemurafenib, Vinorelbine, Vismodegib, Vorinostat, ZSTK474, and any combination thereof.

6. A method for delivering a drug or a bioactive agent to a subject in need thereof, comprising:
providing a pharmaceutical composition comprising:
the toroidal mixed nanoparticle of claim 1;
an effective amount of the drug or the bioactive agent conjugated to the toroidal mixed nanoparticle; and
a pharmaceutically acceptable excipient;
administering the pharmaceutical composition to the subject.

7. The method of claim 6, wherein the subject suffers from cancer.

8. A method for preparing a toroidal mixed micelle nanoparticle, comprising:
forming a solution of a first polymer and a second polymer, wherein the first polymer is d-α-tocopherol polyethylene glycol succinate, and the second polymer is a poly-γ-benzyl-1-glutamate having cleavable benzyl groups;
performing a solvent exchange on the solution to form a mixed micelle nanoparticle; and
removing a portion of the benzyl groups from the second polymer to make the second polymer charged and to form the toroidal mixed micelle nanoparticle.

9. The method of claim 8, wherein the mixed micelle nanoparticle is reacted with acid or base to remove the portion of the benzyl groups from the second polymer.

10. The method of claim 9, wherein the mixed micelle nanoparticle is reacted with base for 2 to 72 hours.

11. The method of claim 8, wherein about 10% to about 50% of the benzyl groups are removed from the second polymer.

\* \* \* \* \*